(12) United States Patent
Ogawa et al.

(10) Patent No.: US 7,688,449 B2
(45) Date of Patent: Mar. 30, 2010

(54) MICROCHIP TESTING DEVICE

(75) Inventors: Yoshimasa Ogawa, Himeji (JP);
Kazuyuki Kaneda, Himeji (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 20 days.

(21) Appl. No.: 11/769,886

(22) Filed: Jun. 28, 2007

(65) Prior Publication Data
US 2008/0002178 A1 Jan. 3, 2008

(30) Foreign Application Priority Data
Jun. 30, 2006 (JP) ............... 2006-182626

(51) Int. Cl.
*G01N 21/00* (2006.01)
(52) U.S. Cl. .............. 356/442; 436/164; 436/177; 422/82.09
(58) Field of Classification Search .............. 356/237.2, 356/39, 432–444; 422/72, 82.03–82.09, 422/102, 104; 436/164–172, 177; 435/287.1–288.7; 248/636
See application file for complete search history.

(56) References Cited

U.S. PATENT DOCUMENTS

| 4,680,164 | A | * | 7/1987 | Kelln ............... 422/72 |
| 4,814,282 | A | | 3/1989 | Holen et al. |
| 5,478,750 | A | * | 12/1995 | Bernstein et al. ....... 436/164 |
| 6,338,820 | B1 | | 1/2002 | Hubbard et al. |
| 6,339,473 | B1 | * | 1/2002 | Gordon .............. 356/440 |
| 7,029,040 | B2 | * | 4/2006 | Lippoldt et al. ........ 292/201 |
| 2002/0085202 | A1 | | 7/2002 | Gordon |
| 2003/0094502 | A1 | | 5/2003 | Andersson et al. |
| 2003/0219890 | A1 | * | 11/2003 | Gordon et al. ........ 435/287.2 |
| 2006/0091085 | A1 | * | 5/2006 | Kobayashi et al. ........ 210/787 |

FOREIGN PATENT DOCUMENTS

| EP | 1 669 733 A1 | 6/2006 |
| JP | 2004-109099 A | 4/2004 |
| JP | 2006-110491 A | 4/2006 |

OTHER PUBLICATIONS

European Search Report for Application No. 3P 07 01 2183 Dated Jun. 29, 2009.

* cited by examiner

*Primary Examiner*—Tarifur Chowdhury
*Assistant Examiner*—Michael Lapage
(74) *Attorney, Agent, or Firm*—David S. Safran; Roberts Mlotkowski Safran & Cole, P.C.

(57) ABSTRACT

An absorptiometry microchip testing device with which, after one-time startup, test results of blood analyses are automatically obtained without a special tester. The microchip testing device has a rotary drive source which can be stopped at a prescribed angle; a centrifugal rotor connected to the rotary drive source via the main shaft; a direction switching mechanism for controlling the main shaft gear; a planetary gear which engages the main shaft gear which is located on the centrifugal rotor; a chip holder which turns together with the planetary gear; a microchip which is held in the chip holder and has a part for measuring absorbance; a light source from which light is incident in the absorbance measuring part of the microchip; a detector which receives light transmitted by the absorbance measuring part; and a controller which controls movements of the rotary drive source and the direction switching mechanism.

4 Claims, 20 Drawing Sheets

Fig. 9 (a)
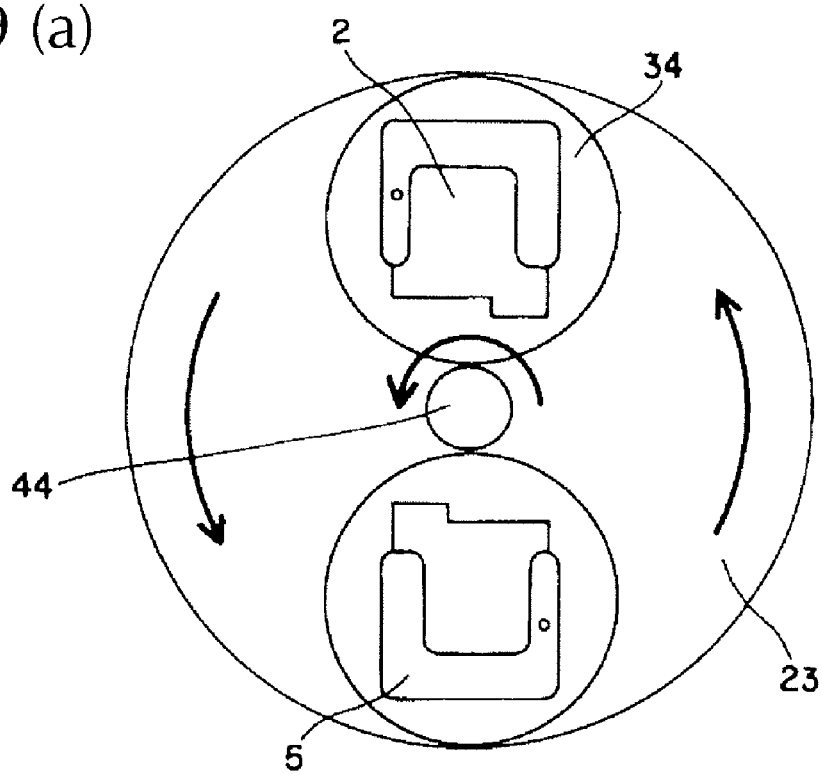
Fig. 9 (b1)
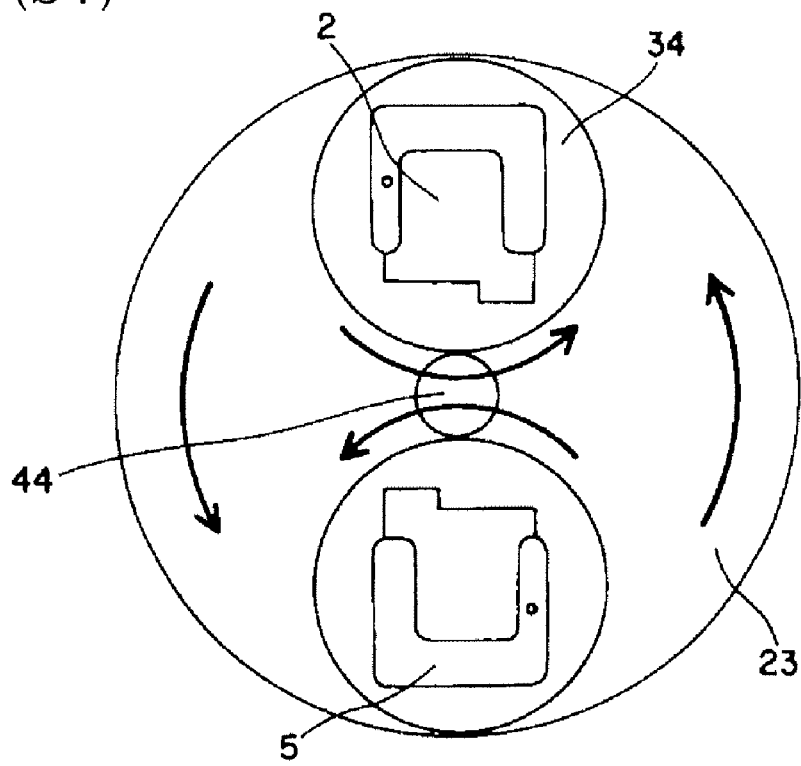

Fig. 10 (b2)
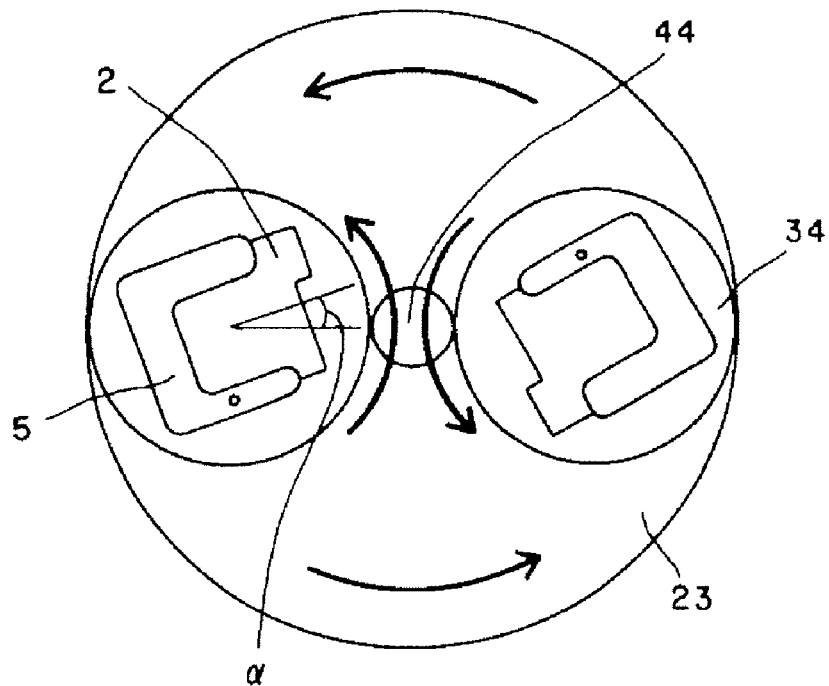
Fig. 10 (b3)
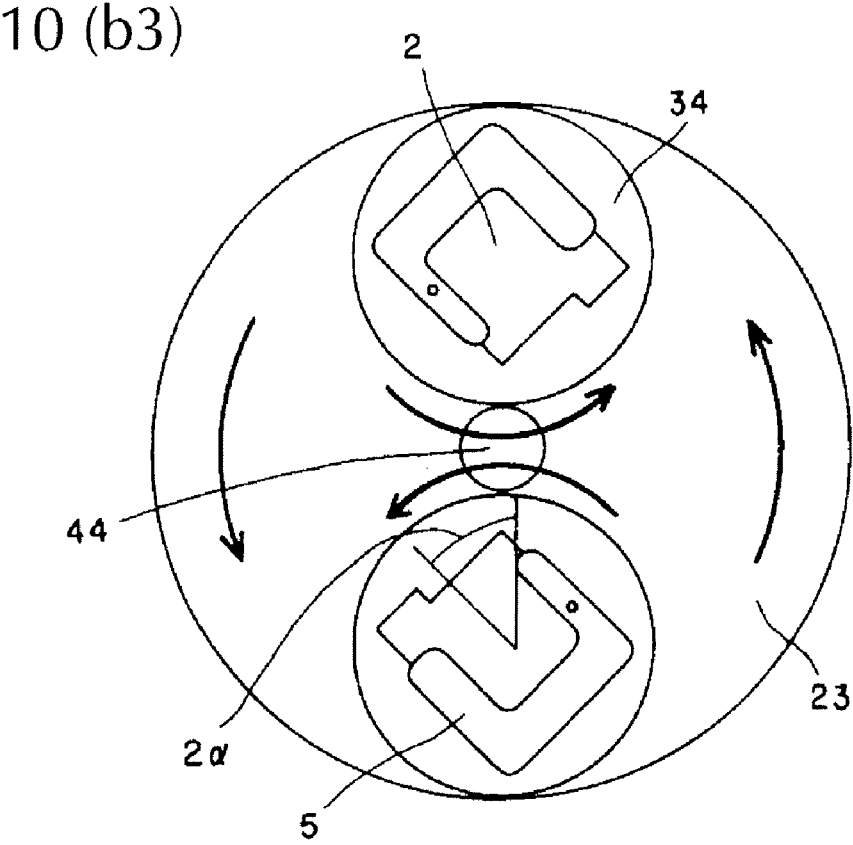

Fig. 11 (b4)
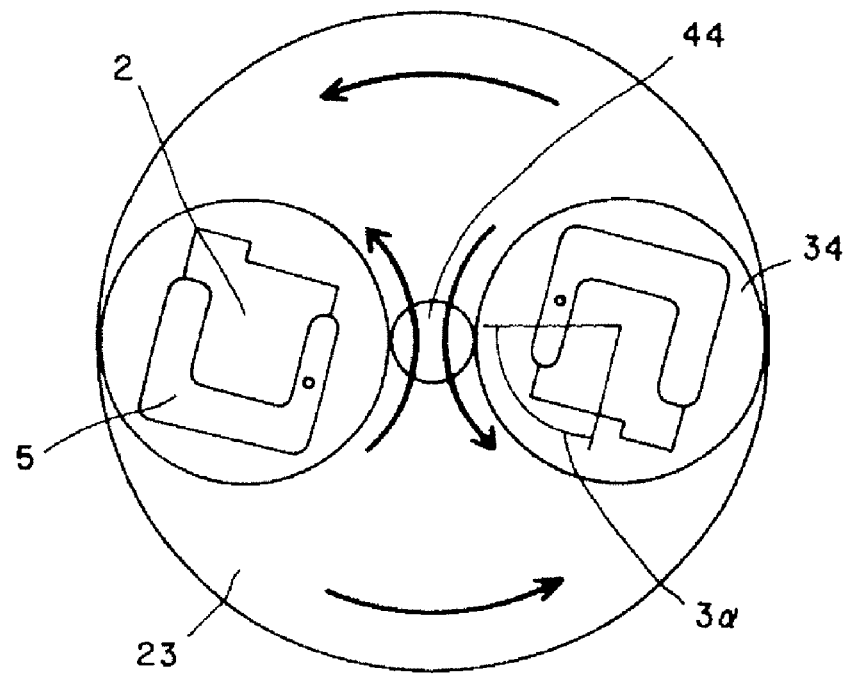
Fig. 11 (b5)
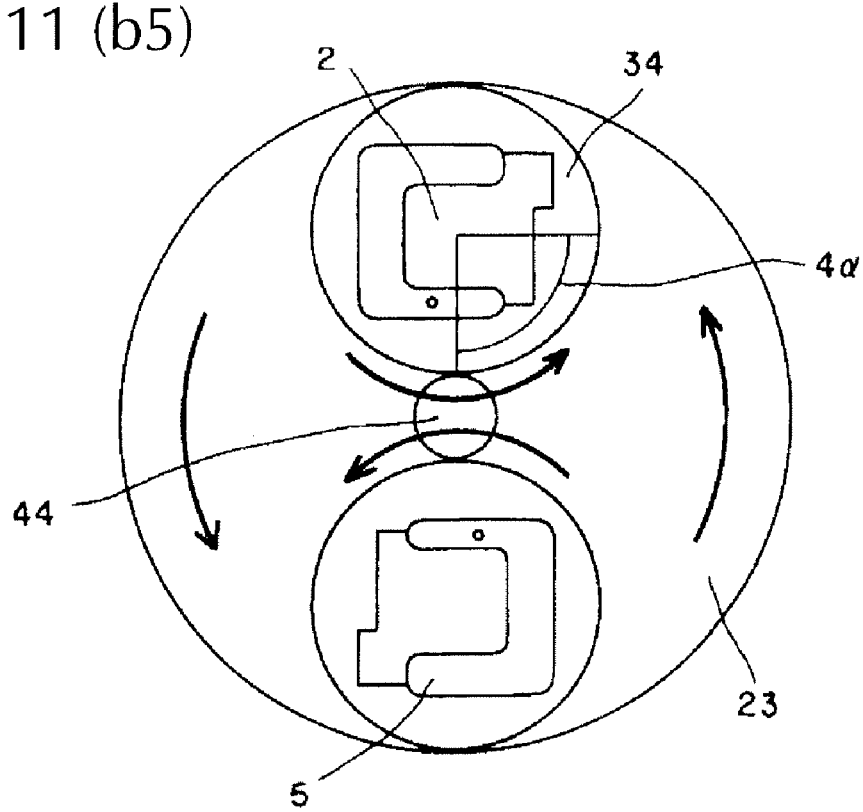

Fig. 20
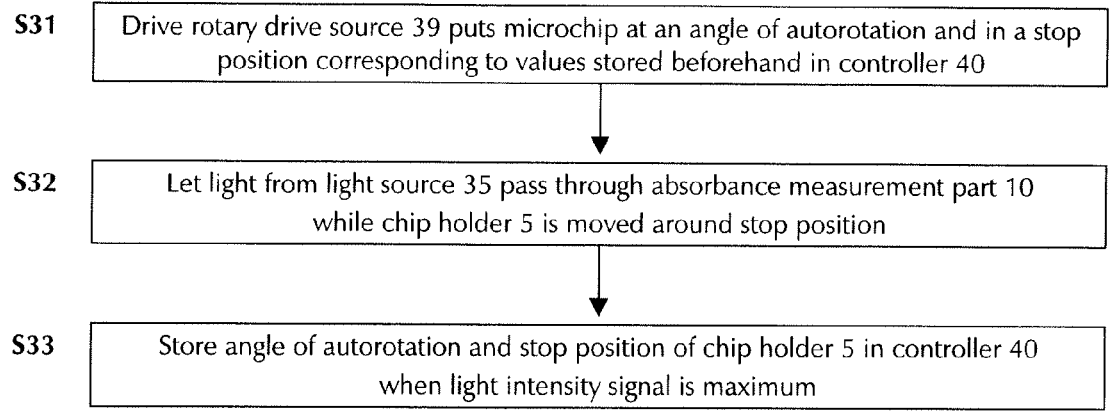
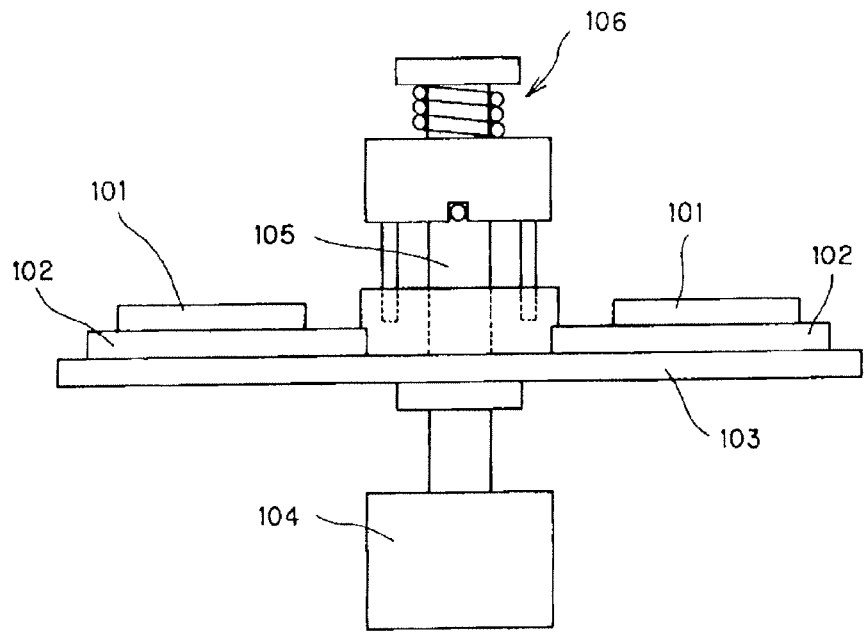
Fig. 21
(Prior Art)

MICROCHIP TESTING DEVICE

BACKGROUND OF THE INVENTION

1. Field of the Invention

The invention relates to a microchip testing device in which blood analyses are carried out by the process of absorptiometry (a diagnostic technique using computerized analysis of absorption rates of photons directed in a focused beam at a test object) using a microchip after completion of a centrifugal process.

2. Description of Related Art

Recently an analysis method using a microchip called "µ-TAS" or "Lab.on a-chip' has been considered in which using precision processing technology of semiconductors and micromachine production technology chemical analyses and the like are performed in a more precise manner as compared to a conventional device. In the case of using µ-TAS for medical fields there are the following and similar advantages:

(1) By reducing the amount of sample, such as, for example, blood, the burden on the patient can be reduced.

(2) The amount of reagent can be reduced and the study costs can be reduced.

(3) Since the device is small, the study can be easily carried out.

In an analysis by the absorptiometry process using a microchip, a series of operations which is described below is carried out and the concentration of a desired enzyme which is contained in the blood plasma is measured. These operations are:

(1) Blood which was taken using a painless needle is delivered into the chip.

(2) The blood in the microchip undergoes centrifugal treatment and is separated into plasma and blood cells.

(3) The plasma and reagent are uniformly mixed and a sample liquid is produced therefrom.

(4) The sample liquid is delivered into the part for measuring absorbance.

(5) The sample liquid which was delivered into the part for measuring absorbance is irradiated with light from a light source and the amount of attenuation of light with a certain wavelength is measured.

For example, Japanese Patent Application Publication JP-A-2006-110491 describes a centrifugal device for a microchip in which a microchip filled with blood as the sample is subjected to a centrifugal force, and thus centrifugal separation is performed in which the blood is separated into plasma and blood cells by the difference between specific weights, in which the plasma is mixed with a reagent and a sample liquid produced therefrom, and in which the sample liquid is fed into the part for measuring absorbance. Afterwards the microchip from which the sample liquid was obtained is taken from the centrifugal device for the microchip, the sample liquid which filled the part for measuring absorbance is irradiated with light from a light source and the amount of attenuation of light with a certain wavelength and the concentration of the desired enzyme which is contained in the plasma are measured.

FIG. 21 shows an example of a conventional centrifugal device which is used for blood analyses. This centrifugal device is made such that a chip holder 102 in which the microchip 101 is held, is placed on the centrifugal rotor 103 of the centrifugal device, that the rotation of the rotary drive source 104 is transferred via a main shaft 105 to the centrifugal rotor 103 and that a speed of at least 3000 rpm is produced by the rotary drive source 104.

In conducting an analysis by the absorptiometry process using this centrifugal device, first the microchip 101 in the chip holder 102 is placed on the centrifugal rotor 103, the centrifugal rotor 103 is turned and the blood is separated into plasma and blood cells. Next, the chip holder is turned automatically by the switching mechanism of the centrifugal direction 106. Afterwards the centrifugal rotor 103 is turned again to switch the direction of the centrifugal force which is being applied to the microchip 101. At this point, the plasma is mixed with the reagent, a sample liquid is thus produced and the sample liquid is fed into the part for measuring absorbance. Afterwards the microchip 101 is taken from the centrifugal device, it is held in the device for testing absorbance (not shown), the sample liquid which has filled the part for measuring absorbance is irradiated with light from a light source and the amount of attenuation of light with a certain wavelength and the concentration of the desired enzyme which is contained in the plasma are measured.

In the conventional centrifugal device as shown in FIG. 21, however, to conduct the analysis by the absorptiometry process, the microchip had to be removed from the centrifugal device, placed in the device for testing absorbance, the part for measuring absorbance of the microchip had to be irradiated with light from the light source, and the amount of attenuation of light with a certain wavelength had to be measured. The diameter of the cross section which is perpendicular to the optical axis of the part for measuring absorbance of the microchip is, for example, a 1.0 mm. Irradiation with light had to be exact to prevent scattered light travelling to outside the part for measuring absorbance of the microchip. If the microchip is not held exactly in the device for testing absorbance, the optical path of the light which is transmitted by the part for measuring absorbance is slightly lengthened so that the amount of light attenuation increases. It was possible for this to lead to incorrect test results. Since, in this way, for analyses by the absorptiometry process, a precise device for testing absorbance is required, it was difficult to carry out analyses by the absorptiometry process of the microchip on the centrifugal rotor of the centrifugal device.

In the above described conventional centrifugal device, it was necessary to carry out centrifugal separation by rotation of the centrifugal rotor, afterwards to actuate the switching mechanism of the centrifugal direction by a tester or the like, to subject the chip holder to autorotation, switch the centrifugal direction, turn the centrifugal rotor again, furthermore, to remove the microchip from the centrifugal device by the tester or the like, place it in the device for testing absorbance and test it. The tester or the like was never able to leave the centrifugal device and the device for testing absorbance. Therefore, special testers or the like had to be delegated for conducting blood analyses by the absorptiometry process, with the resulting disadvantage of additional personnel costs and the like.

SUMMARY OF THE INVENTION

The invention was devised to eliminate the above described disadvantages in the prior art. Thus, a primary object of the invention is to devise a microchip testing device in which blood analyses by the absorptiometry process with the microchip are performed on the centrifugal rotor of a centrifugal device, in which after one-time startup, the test results of blood analyses are automatically obtained, and in which a special tester or the like is not required.

The above described object is achieved by the following approaches.

The object is achieved according to a first approach of the invention in a microchip testing device by the following features:

a rotary drive source which can be stopped at a prescribed angle;

a centrifugal rotor which is connected to the main shaft which is turned by the above described rotary drive source;

a switching mechanism of the centrifugal direction for controlling the concentric rotatable object which is freely fixed on the above described main shaft;

a planetary revolution object which engages the above described concentric rotatable object which is located on the above described centrifugal rotor;

a chip holder which turns together with the above described planetary revolution object;

a microchip which is held in the above described chip holder and which has a part for measuring absorbance;

a light source from which light is incident in the part for measuring absorbance of the above described microchip;

a detector which receives the light which has been transmitted by the above described part for measuring absorbance; and a controller which controls the movements of the above described rotary drive source and the above described switching mechanism of the centrifugal direction.

The object is achieved according to a second approach of the invention in a microchip testing device according to the first approach in that the above described switching mechanism of the centrifugal direction executes an alternative switching operation in the following modes:

a centrifugation mode in which the above described concentric rotatable object is connected to the above described rotary drive source and in which the planetary revolution object is turned without autorotation; and a switching mode of the centrifugal direction in which the above described concentric rotatable object is connected to a measurement chamber and is attached to it and in which the above described planetary revolution object is subjected to planetary motion in which it is turned with simultaneous autorotation.

The object is achieved according to a third approach of the invention in a microchip testing device according to the first or second approach in that underneath the above described centrifugal rotor there are a supporting part which moves up and down, and a supporting part drive part for driving the above described supporting part and that when the above described supporting part moves up the above described centrifugal rotor is supported by the above described supporting part.

The object is achieved according to a fourth approach of the invention in a microchip testing device according to the third approach in that the above described controller is designed to first move the above described supporting part down, afterward start rotation of the above described centrifugal rotor and after stopping the above described centrifugal rotor to move the above described supporting part up.

The object is achieved according to a fifth approach of the invention in a microchip testing device according to the first or second approach in that in the above described test device there are a lock part for attaching the access cover in the locked closed state, and a lock part driving part for driving the above described lock part and that the above described access cover maintains the closed state by the above described locking part.

Action of the Invention

Analyses by the absorptiometry process in a microchip can be carried out on the centrifugal rotor by the microchip testing device in accordance with the invention since it comprises the following:

a rotary drive source which can be stopped at prescribed angle based on the display of a controller;

a light source from which light is incident in the part for measuring absorbance of the microchip which is held in the chip holder; and a detector which receives the light which has been transmitted by the part for measuring absorbance and which computes the test result based on the amount of light received.

Furthermore, since the device has a controller for controlling the rotary drive source, the switching mechanism of the centrifugal direction and the part for measuring absorbance, a test result is automatically obtained by operation of the microchip testing device so that special testers need not be delegated.

The invention is further described below with reference to the accompanying drawings.

BRIEF DESCRIPTION OF THE DRAWINGS

FIGS. 9(a) & 9(b1) each show a schematic of the operating conditions of the centrifugal rotor, of the main shaft gear and of a planetary gear of the microchip testing device relative to one another;

FIGS. 10(b2) & 10(b3) each show a schematic of the operating conditions of the centrifugal rotor, of the main shaft gear and of the planetary gear of the microchip testing device relative to one another;

FIGS. 11(b4) & 11(b5) each show a schematic of the operating conditions of the centrifugal rotor, of the main shaft gear and of the planetary gear of the microchip testing device relative to one another;

FIG. 20 is a flow chart of the sequence of actuation of treatment in which the angle of autorotation of the chip holder in which the aperture part of the chip holder is located at a position corresponding to a detector and the stop position of the centrifugal rotor are corrected; and FIG. 21 is a schematic representation of an example of a conventional centrifugal device which is used for blood analyses.

DETAILED DESCRIPTION OF THE INVENTION

Figure 1:
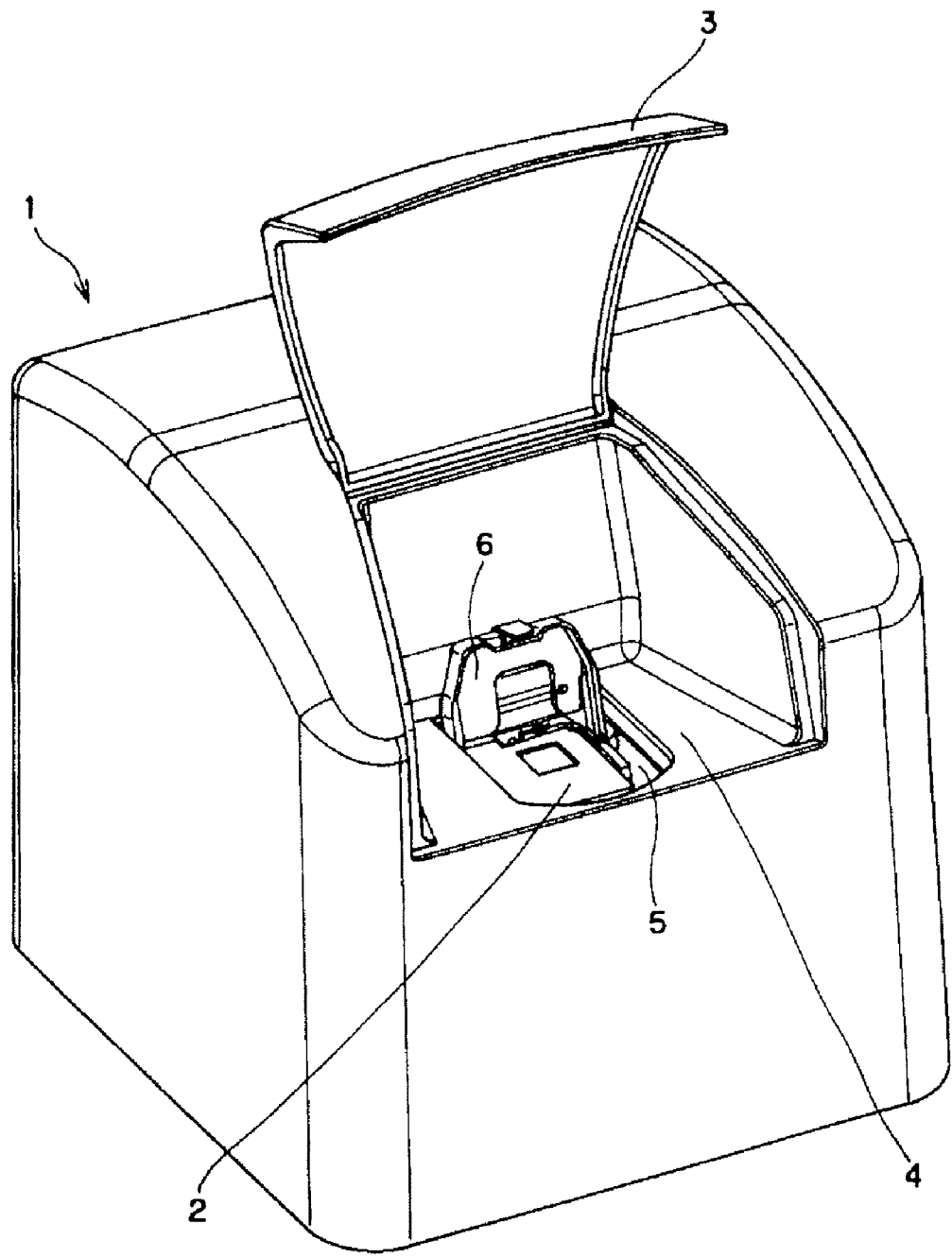
FIG. 1 is a perspective view of the microchip testing device in accordance with the invention.

FIG. 1 is an external view of a microchip testing device in accordance with the invention. As is shown in the drawings, the outside of the microchip testing device is comprised of a body 1 in the form of a rectangular parallelepiped in which there is an access cover 3 which is used for insertion and removal of the microchip 2. The cover 3 is attached, for example, by a hinge such that it can be opened or closed. When the microchip 2 is to be inserted into the microchip testing device, the access cover 3 is opened, the microchip 2 is placed on the chip holder 5 in a microchip insertion part 4, the cover 6 is closed, attached and the access cover 3 is closed.

Figure 2:
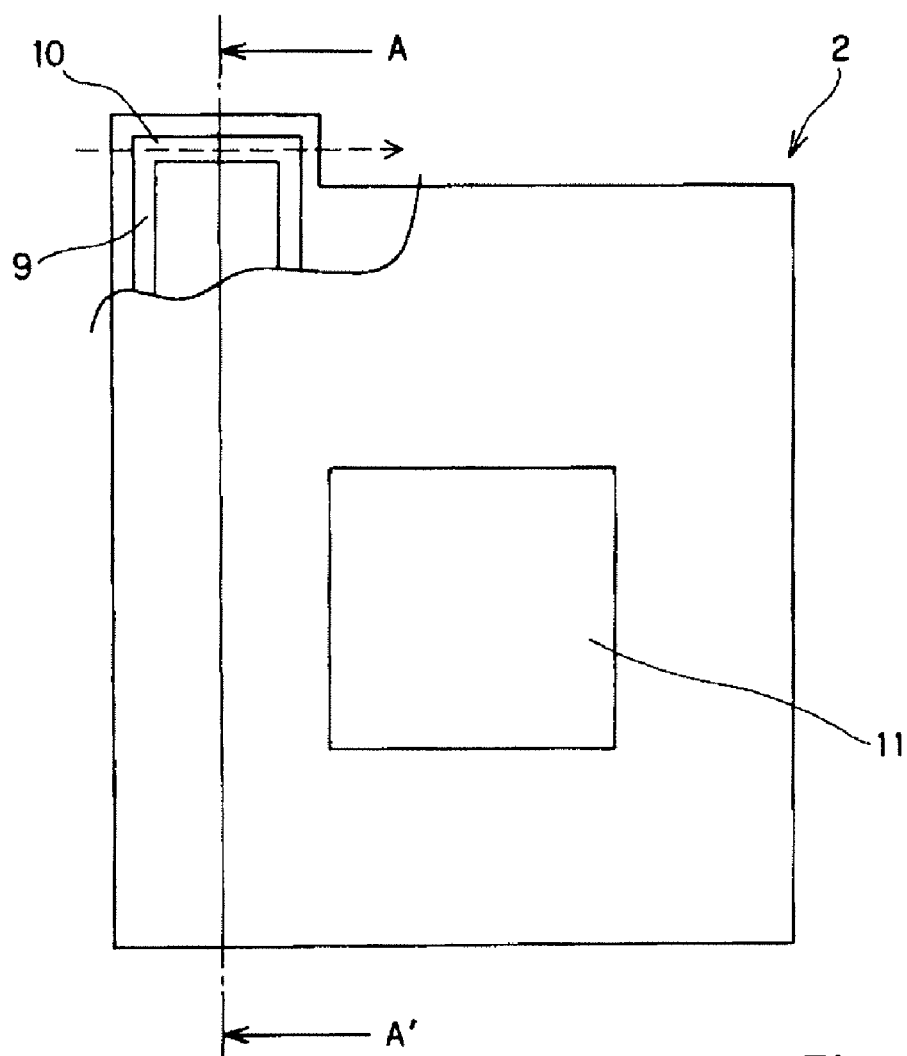
FIG. 2(a) is a top view of the microchip which is held in a chip holder of a microchip testing device.
FIG. 2(b) is a partial cross-sectional view of the microchip which is held in a chip holder of a microchip testing device.
Figure 2:
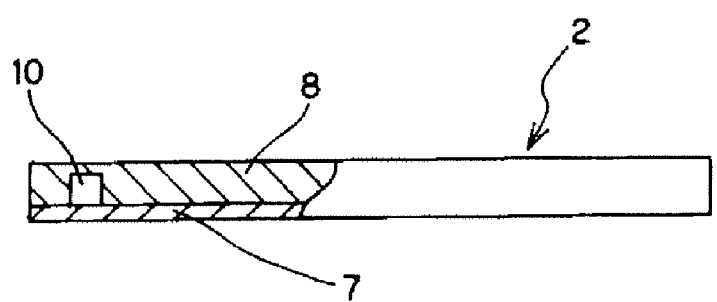

FIG. 2(a) is a top view of the microchip 2 which is held in the chip holder 5 of the microchip testing device. FIG. 2(b) is a cross section according to A'-A' in FIG. 2(a). As is shown in FIG. 2(b), the microchip 2 is formed of a light-shielding resin 7 and a transparent resin 8 that have been cemented to one another. As is shown in FIG. 2(a), within the microchip 2 for individual lot testing, a groove 9 is formed in the transparent resin 8 which constitutes the passage for the blood as the sample. For example at one site the part for measuring absorbance 10 is formed with a 1 mm angle. At a given site, a reagent or the like (not shown) is added and automatically mixed with a plasma in a given stage of the test, and thus, a sample liquid is obtained which is added to the part for measuring absorbance 10 from which light is transmitted horizontally to the microchip 2, and this analysis is performed using the absorptiometry process. On the surface of the microchip 2, a two-dimensional code 11 is cemented which stores information, such as the serial number, shelf life of the chip, type of measurement lots, position of the part for measuring absorbance 10, variance of the reagent lot per microchip and the like.

Figure 3:
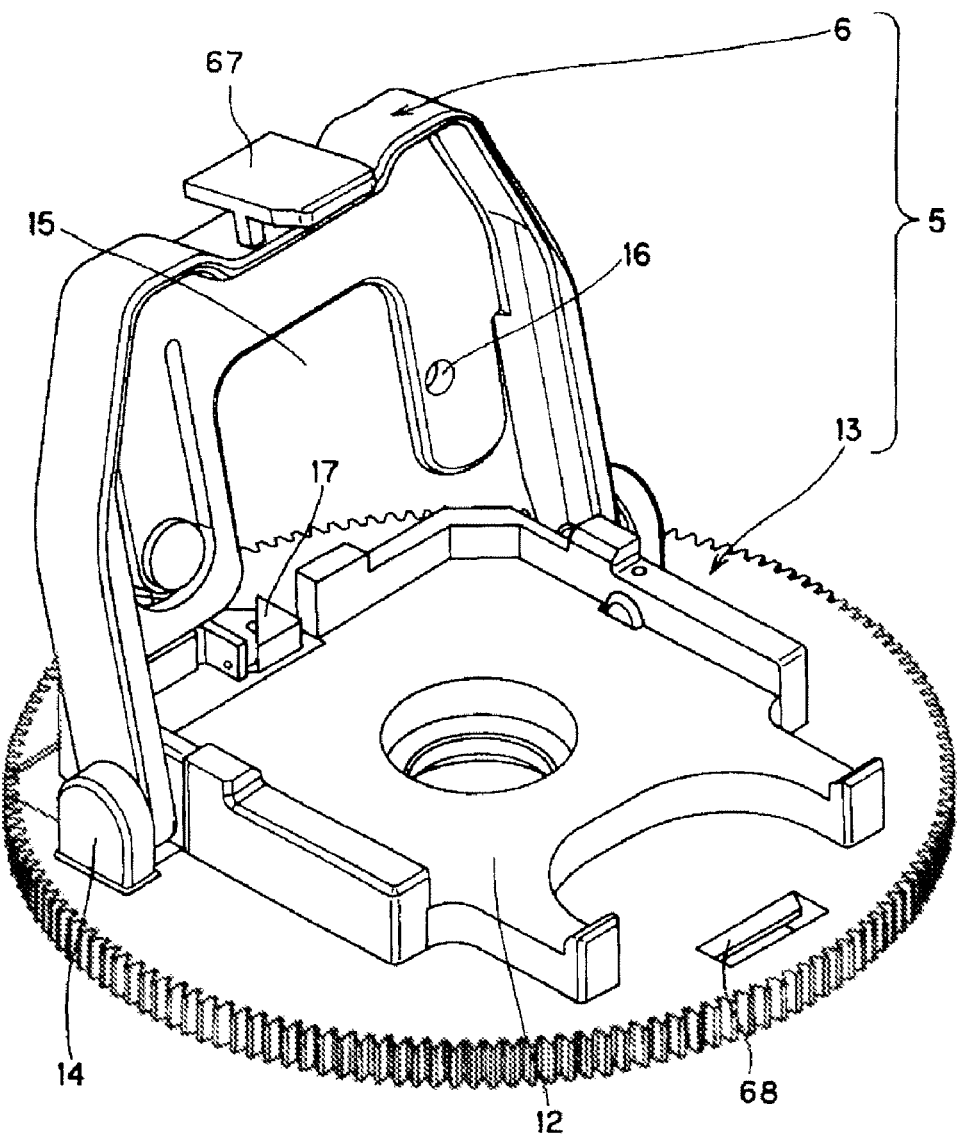
FIG. 3 is a perspective view of the chip holder in which the microchip is held.

FIG. 3 is a perspective view of the chip holder 5 in which the microchip 2 is held. As is shown in FIG. 3, the chip holder 5, which is formed, for example, of resin, is comprised of an open box shaped part 13 which has a chip holding space 12 in which the microchip 2 is held, and a cover 6 which positions and holds a microchip 2 (not shown) at a given position. The cover 6 is attached at articulation points on each of opposite sides by a respective hinge 14. In the cover 6, a code reader window 15 is provided for enabling the two-dimensional code 11 attached to the microchip 2 to be read from the outside and a sample quantity sensor reading opening 16 for checking whether the amount of sample added to the microchip 2 is sufficient or not.

The cover 6 is held closed by a hook 67 of the cover 6 being hooked in a hook attachment opening 68 of the box 13 so that even when centrifugal force is applied to the microchip 2, the cover 6 does not open. The attachment is such that the cover 6 does not open even when the chip holder 5 is exposed to a centrifugal force of over 400 G, this centrifugal force being applied to separate blood as the sample which has been added to the microchip 2 into plasma and blood cells, for example, since one minute of rotation at 3000 rpm is needed.

Furthermore, it is necessary for the microchip 2 to be positioned and attached in a stationary manner in the chip holding part 12 with an accuracy within ±0.2 mm. This is because, after centrifugal treatment in the state in which the microchip 2 continues to be held in the chip holder 5, the part for measuring absorbance 10 must be exactly irradiated with light from a light source (not shown) and the amount of attenuation of the light with a certain wavelength must be exactly measured, the diameter of the cross section of the microchip 2 which is perpendicular to the optical axis of the part for measuring absorbance 10 being, for example, a 1.0° angle.

Figure 4:
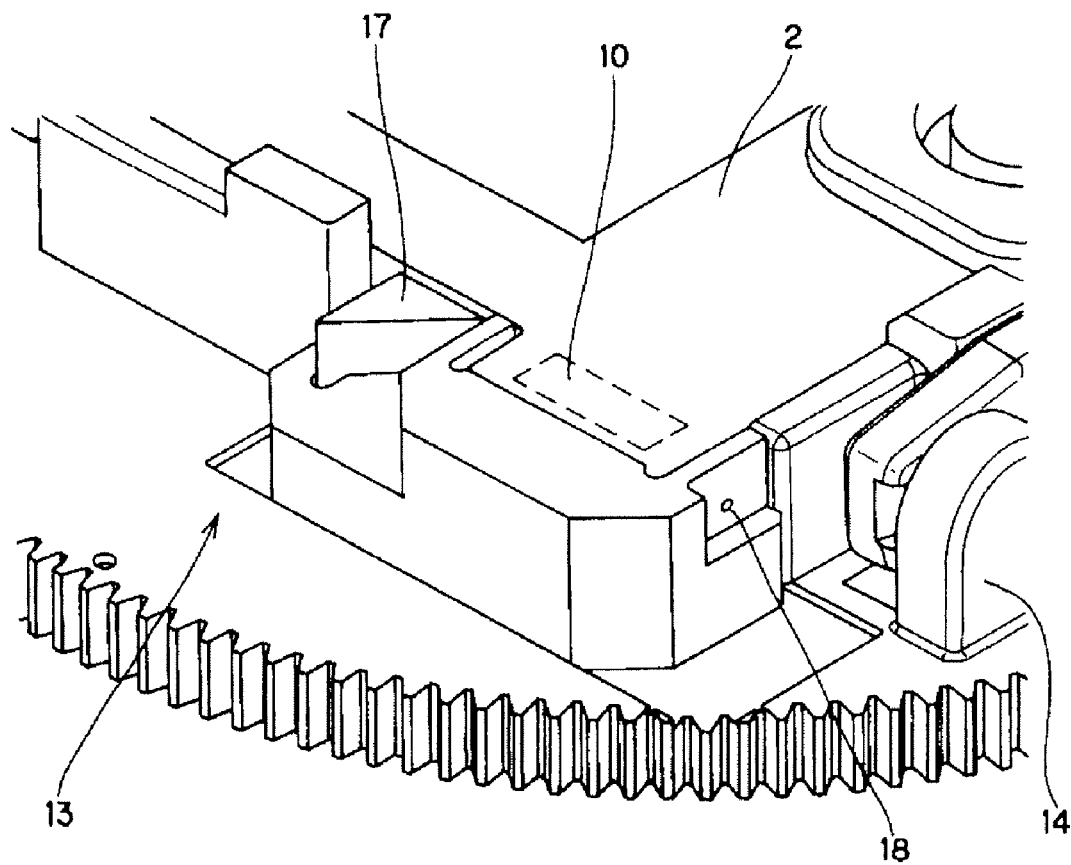
FIG. 4 is an enlarged view of a portion of the chip holder shown in FIG. 3.

FIG. 4 is an enlargement of the chip holder 5 shown in FIG. 3 in a partial view which is used to show the light transmission in the part for measuring absorbance 10 of the microchip 2 which is held in the chip holder 5. As is shown in FIG. 4, on the side of the box-shaped part 13 of the chip holder 5, an aperture part 18 is formed by which the light from a light source (not shown) is incident in the part for measuring absorbance 10 of the microchip 2. The aperture part 18 has a shape which corresponds to the cross section of the part for measuring absorbance 10 of the microchip 2. It is, for example, an opening with a diameter of 0.6 mm and is used for shielding so that no excess light is incident in the part for measuring absorbance 10. The light incident from the aperture 18 is transmitted by the part for measuring absorbance 10 and emerges from a light passage opening which is not shown in the drawings. The emerging light is reflected by a mirror 17 and is received by a detector which is not shown in the drawings.

Figure 5:
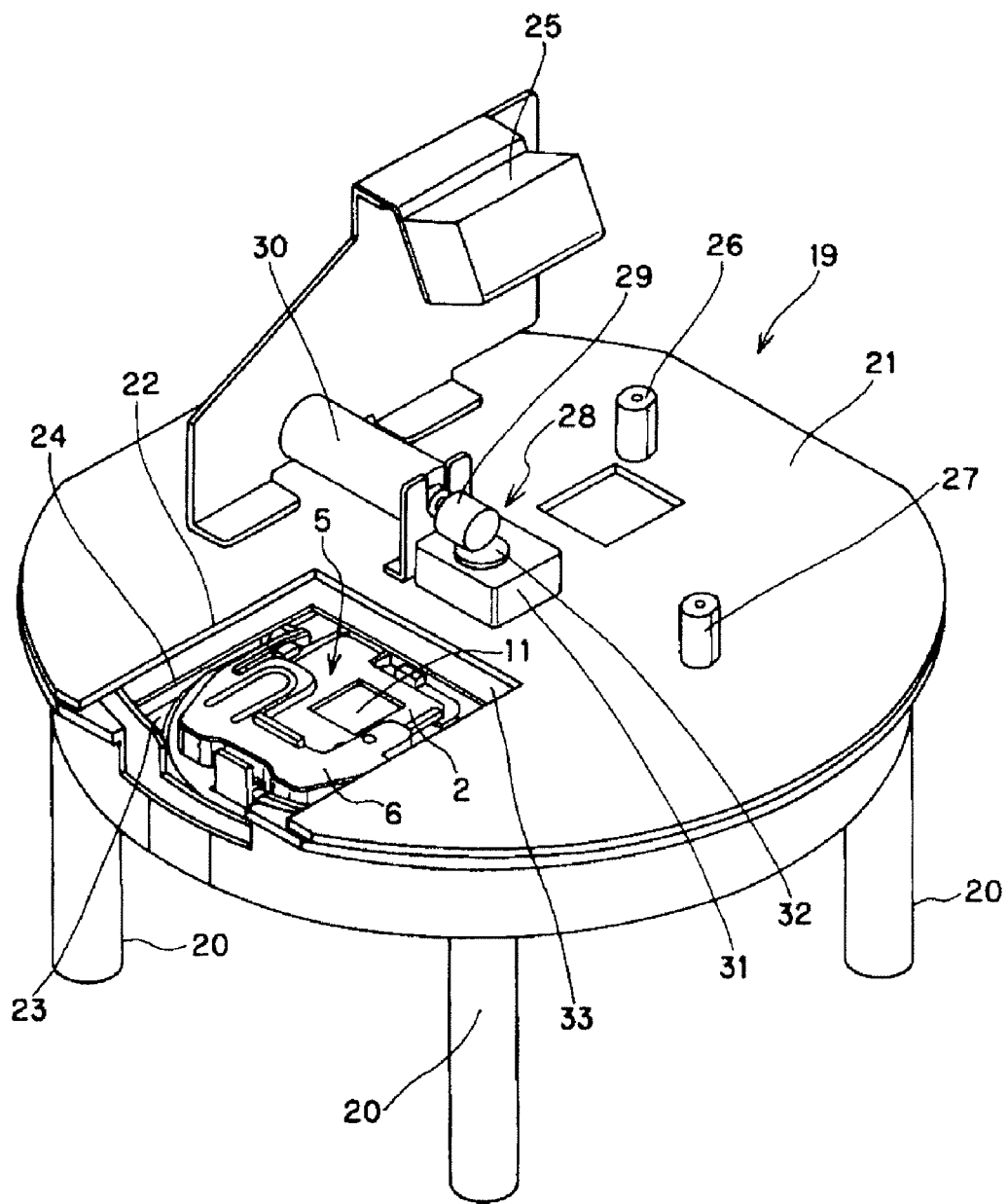
FIG. 5 is an outside view of a measurement chamber which is located in the body of a microchip testing device.

FIG. 5 is an external view of a measurement chamber 19 which is located within the body 1 of the microchip testing device. As is shown in FIG. 5, the measurement chamber 19 is made in the form of a hollow disk and is supported, for example, by four legs 20 which are attached in the main part of the device. On the top side 21 of the measurement chamber 19, at the point which corresponds to the microchip insertion part 4 of the body 1 shown in FIG. 1, there is a measurement chamber-chip insertion window 22. Furthermore, within the measurement chamber 19, there is a centrifugal rotor 23 in the form of a hollow disk. On the top side of the centrifugal rotor 23, at the point which corresponds to the microchip insertion part 4 of the body 1, there is a centrifugal rotor chip insertion window 24. In this way, proceeding from the microchip insertion part 4, the chip holder 5 can be directly controlled when the access cover 3 is opened.

Furthermore, a code reader 25 for reading the two-dimensional code 11 which is attached to the microchip 2, a sample quantity sensor 26 for measuring the amount of blood added to the microchip 2, and a reflection sensor 27 for determining the direction of the microchip 2 are attached on the top side 21 of the measurement chamber 19. The code reader 25, the sample quantity sensor 26 and the reflection sensor 27 can be installed anywhere. However, it is advantageous to place them at locations which are remote from the measurement chamber chip insertion window 22 to avoid scattered light which is incident in the measurement chamber 19 from the measurement chamber chip insertion window 22. Furthermore, by placing the code reader 25, the sample quantity sensor 26 and the reflection sensor 27 at a location which corresponds to the microchip 2 located at a given point, two to three measurements can be taken at the same time when the microchip 2 is at this location.

The code reader 25 is designed to read the two-dimensional code 11 which is attached to the microchip 2. Since the two-dimensional code 11 is read as an image, it is located at a distance from the measurement chamber 19 for focusing of the lens and for similar reasons. Based on the information stored in the two-dimensional code 11 the rotary speed, rotation time and centrifugal direction for the microchip 2 can be determined.

The sample quantity sensor 26 is designed to confirm whether the microchip 2 contains enough blood or not. A wavelength which is easily absorbed by blood, for example, light of roughly 550 nm wavelength, emerges from the sample quantity sensor 26 in the direction toward the passage of the microchip 2. The intensity of the reflection light from it is now measured. When the microchip 2 contains enough blood, the light is absorbed by the blood and hardly any reflection light is detected by the sample quantity sensor 26. When there is not enough blood in the microchip 2, the light is reflected from the bottom surface of the blood passage of the microchip 2. The reflection light is received by the sample quantity sensor 26, with it having been hardly attenuated. In this way, based on the intensity of the light received by the sample quantity sensor 26 it can be assessed whether there was enough blood in the microchip 2 or not.

The reflection sensor 27 is also designed to determine the direction of the microchip 2. If a vibration or the like is applied to the microchip testing device, and thus, a safety stop device is operated, or if as a result of the sudden failure of the current source, the treatment of the microchip 2 is suddenly stopped or in similar cases, the direction of the microchip 2 is confirmed by the reflection sensor 27 and the device is restarted.

Furthermore, on the top side 21 of the measurement chamber 19, a cam 29 of a switching mechanism for the centrifugal direction 28, a direction reversing motor 30 and a slide bearing 31 are installed. As is described below, a vertical shaft 32 which has been pressed down by the cam 29 moves within the slide bearing 31, sliding up, when the direction reversing motor 30 is being driven and the cam 29 is turned by 180°. Thus, the centrifugation mode is switched to the switching mode of the centrifugal direction. Also, if the direction reversing motor 30 is driven and the cam 29 turned by 180°, the cam 29 presses the vertical shaft 32 down again, so that the vertical shaft 32 moves down by sliding in the slide bearing 31, by which the switching mode of the centrifugal direction is switched to the centrifugation mode.

Figure 6:
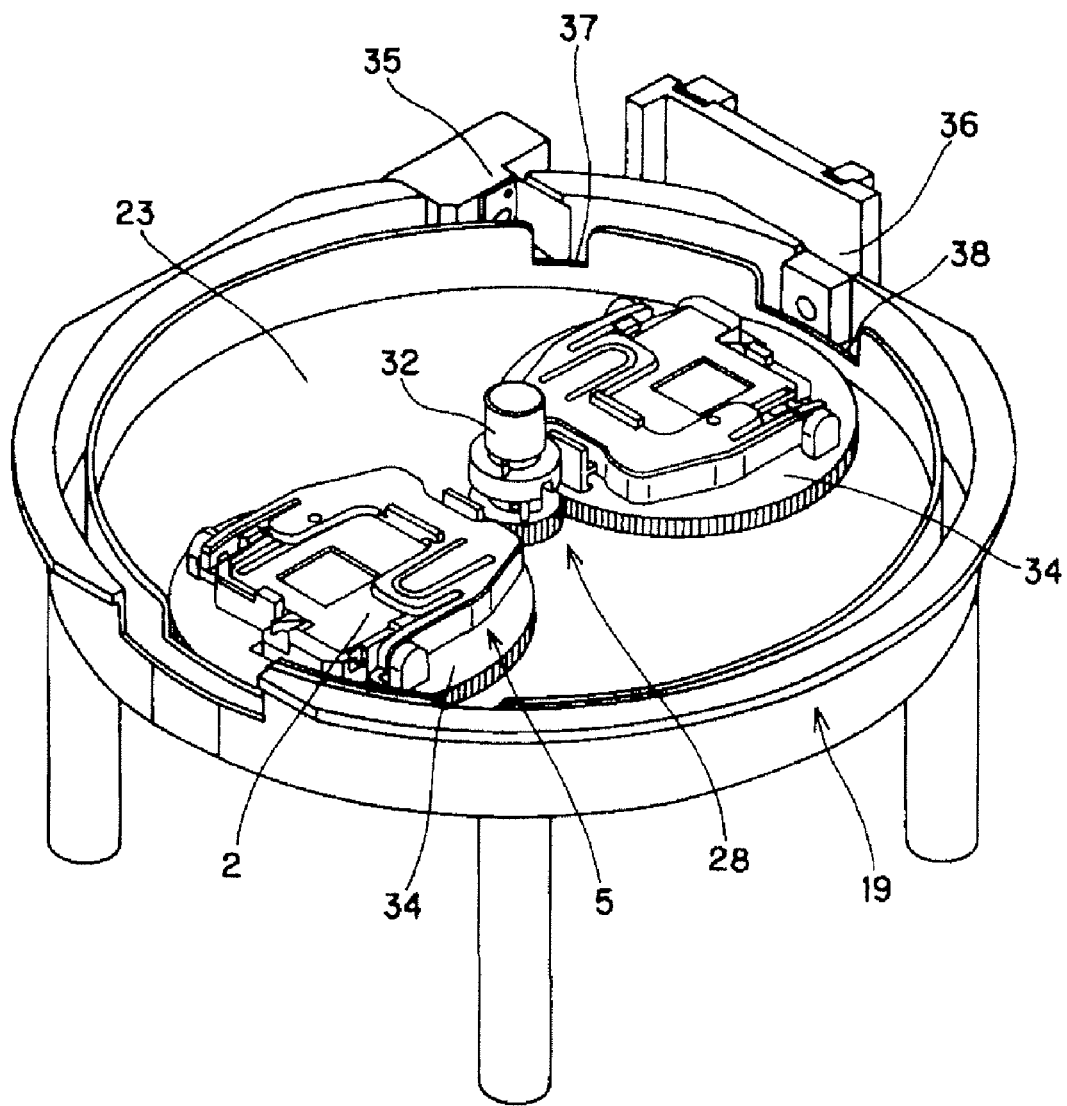
FIG. 6 is an outside view of the inner structure of the measurement chamber as shown in FIG. 5, of which the upper side of the measurement chamber and the upper side of the centrifugal rotor have been dismounted.

FIG. 6 shows the internal structure of the measurement chamber 19 of FIG. 5, from which the top side of the measurement chamber 19 and the top side 33 of the centrifugal rotor 23 have been removed. As is shown in FIG. 6, the switching mechanism for the centrifugal direction 28 in the middle of the centrifugal rotor 23. The microchip 2 is held in the chip holder 5 which is arranged symmetrically to the switching mechanism for the centrifugal direction 28. The chip holder 5 is located on a planetary gear 34 with a toothed edge. The concentric rotatable object and planetary revolution object are, for example, a wheel, in which teeth engage one another, a roller in which rubber rubs against one another by engagement, and the like. A case of using the main shaft gear 44 and a planetary gear 34 is described in which teeth engage one another. Furthermore, the box-shaped part 13 of the chip holder 5 and the planetary gear 34 with the toothed edge can also be formed as separate bodies.

On the side of the measurement chamber 19, there are a light source 35 and a detector 36 arranged as shown in FIG. 4 such that the light emerging from the light source 35 passes through the aperture part 18 of the chip holder 5, is transmitted by the part for measuring absorbance 10 of the microchip 2, is reflected by the mirror 17 of the chip holder 5, and is received by the detector 36 when the microchip 2 is at a given location. On the side of the centrifugal rotor 23 at a point corresponding to the light source 35, there is a light source groove 37 and at a point corresponding to the detector 36 there is a detector groove 38, each of which is arranged such that the passage of the light emerging from the light source 35 and the passage of light reflected by the mirror 17 are not prevented.

The light source 35 can be a xenon lamp, an ultra-high pressure mercury lamp which is advantageously used as a light source of a projector, a metal halide lamp of the short arc type, LED, LD or the like. It is advantageous to use a xenon lamp of the short arc type with a power consumption of 20 W to 75 W because, in this connection, high emission intensity and moreover a point light source can be easily obtained because it also has a continuous spectrum in a wide wavelength range from 250 nm to 1400 nm and because especially in the wavelength range which is often used to measure absorbance (specifically in the wavelength range from 300 nm to 800 nm) a stable radiation spectrum can be obtained without especially bright lines.

The detector 36 receives the light which has been transmitted by the part for measuring absorbance 10 of the microchip 2 and reflected by the mirror 17. Based on the amount of light received by the detector 36, a light intensity signal is output and the test result computed. The detector 36 comprises a light receiving element for which, for example, a silicon photodiode or the like can be used. A silicon photodiode is a light receiving element which has sensitivity for light in the wavelength range from 300 nm to 1100 nm. This means that a light intensity signal is output based on the amount of light received by the detector 36, the amount of reduction of light with this certain wavelength is measured and the concentration of the detection object component in the sample liquid of the part for measuring absorbance 10 is computed.

Figure 7:
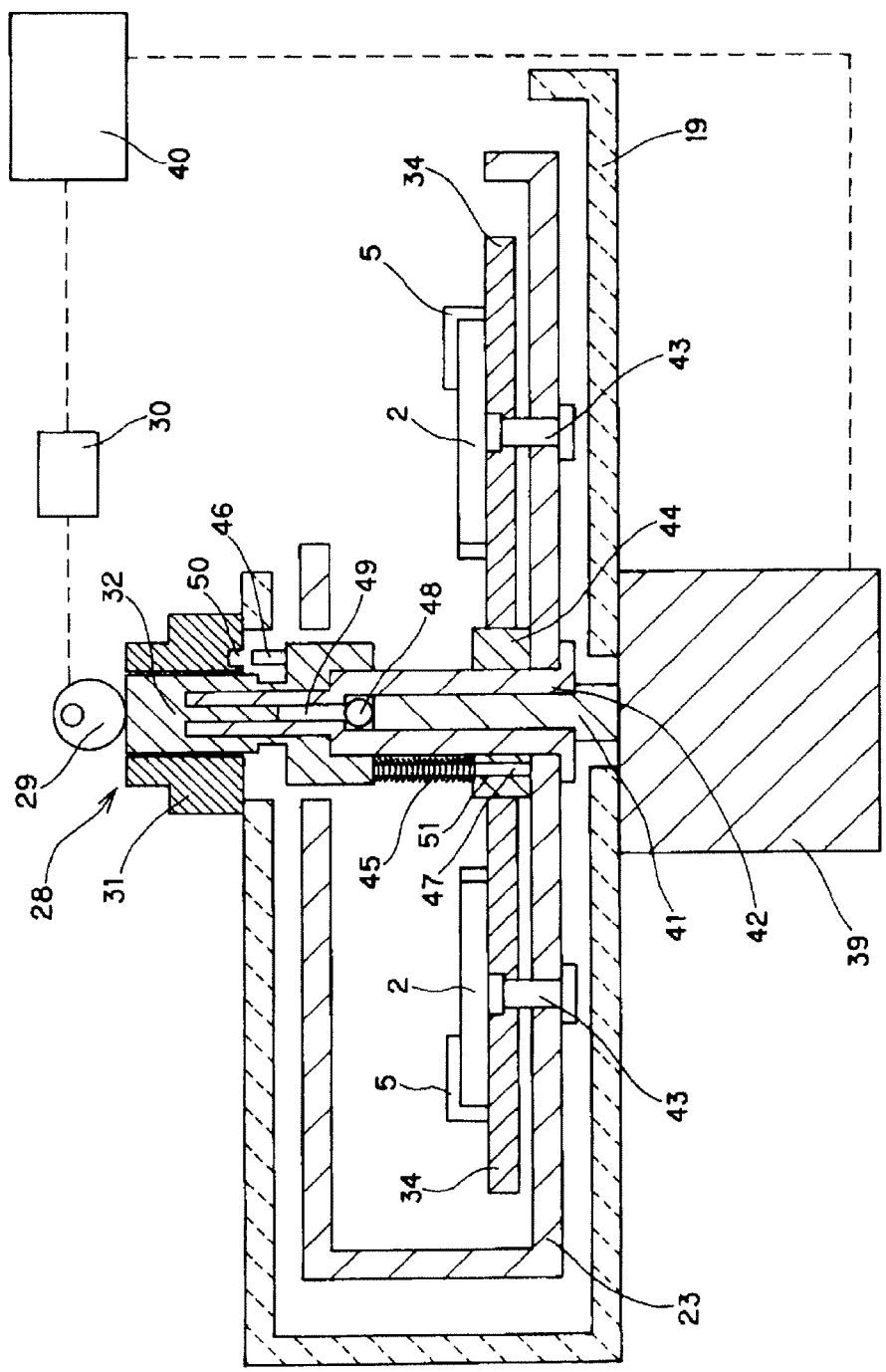
FIG. 7 is a cross-sectional view of the inner structure of the body of the microchip testing device.

FIG. 7 is a cross-sectional view of the internal structure of the body 1 of the microchip testing device. As is shown in FIG. 7, the rotary drive source 39 is mounted in the measurement chamber 19 and is controlled by the controller 40. The switching mechanism of the centrifugal direction 28 is controlled by the drive of the direction reversing motor 30 by the controller 40. From the upper center region of the rotary drive source 39 an axis of rotation 41 runs in which the main shaft 42 is attached for example by a screw connection such that the axis of rotation 41 is jacketed by it. In this way, the main shaft 42 is turned by the rotary drive source 39. The centrifugal rotor 23 is connected to the main shaft 42, being attached, for example, on the main shaft 42 by a screw connection. In this way, rotary motion is transferred to the axis of rotation 41, the main shaft 42, and the centrifugal rotor 23 from the rotary drive source 39 and they turn integrally with one another. The planetary gear 34 maintains the state in which it is, for example, 0.2 mm away from the centrifugal rotor 23. It is attached to the planetary main shaft 43 which is mounted in the centrifugal rotor 23 by a rotary screw connection of the planetary gear 34.

The rotary drive source 39 comprises a DC motor (not shown) and a coder (also not shown), is controlled by the controller 40, and can keep the centrifugal rotor 23 at a prescribed angle with an accuracy from 0.01° to 0.1°. This means that the microchip 2 can be positioned, turned and held in the circular peripheral direction with a precision from 0.05 to 0.1 mm. The coder irradiates a rotary disk, in which on the periphery of the circle there are a host of optical slits parallel to one another, with light through the slits, determines this light, and in this way, measures the angle of rotation and the rotary speed by the controller 40. Based on this measured value, the controller 40 sends an ON/OFF signal to the DC motor, by which the rotary drive source 30 is turned with the desired speed and is stopped at the desired angle. When rotation stops, the controller 40 can maintain the stop position by rotating the DC motor in the blocking direction when it is measured that the coder has moved slightly from the stop position. Furthermore, the rotary drive source 39 can also be a stepping motor. However, due to the low rotary efficiency of the stepping motor, it is necessary to engineer with consideration of heat generation when the rotary speed increases, and of a small torque in high speed rotation.

The main shaft gear 44 which engages a planetary gear 34 is mounted freely fitting on the main shaft 42. The main shaft 42 and the main shaft gear 44 can turn independently of one another. Above the main shaft 42 is a vertical shaft 32 of the switching mechanism of the centrifugal direction 28; switching mechanism 28 comprises a cam 29, a slide bearing 31, a vertical shaft 32, a spring 45, an upper engagement pin 46, a lower engagement pin 47, a main shaft coupling pin 48, and a direction reversing motor 30. The center axis of the vertical shaft 32 is inserted into the middle groove 49 of the main shaft 42. The vertical shaft 32 is used to increase the accuracy with which the main shaft 42 is brought into agreement with the center axis of the switching mechanism of the 28. The vertical shaft 32 is provided with an upper engagement pin 46 and a lower engagement pin 47. The slide bearing 31 is provided with a groove 50 for the upper engagement pin into which the upper engagement pin 46 is inserted. The main shaft gear 44 is provided with a groove 51 for the lower engagement pin into which the lower engagement pin 47 is inserted. Since the lower engagement pin 47 is inserted into the groove for the lower engagement pin via the spring 45, for the vertical shaft 32, a force directed upward is always applied. However, a compressive force is applied to the top side of the vertical shaft 32 to prevent upward motion of the vertical shaft 32 since its top side borders the cam 29.

Figure 8:
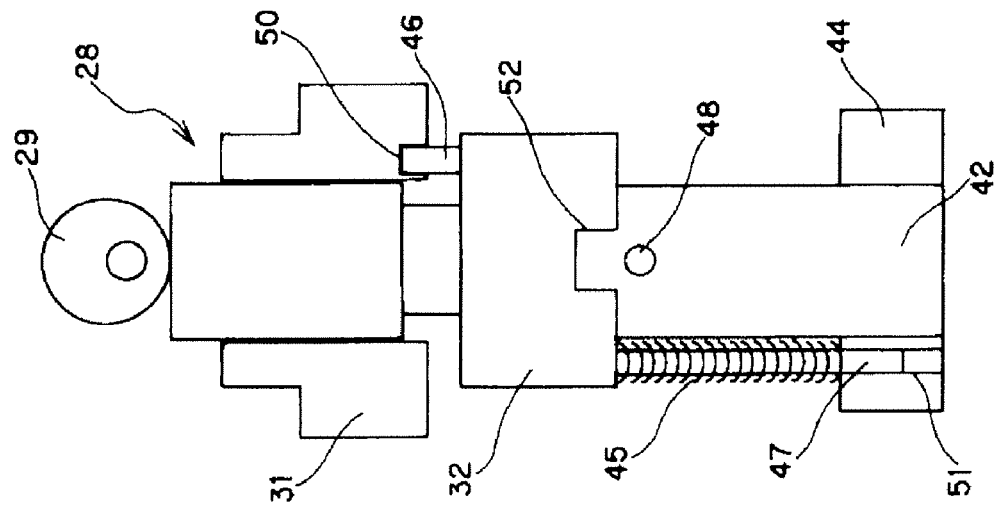
FIGS. 8(a) & 8(b) each show a schematic of the operation of the switching mechanism of the centrifugal direction of the microchip testing device.
Figure 8:
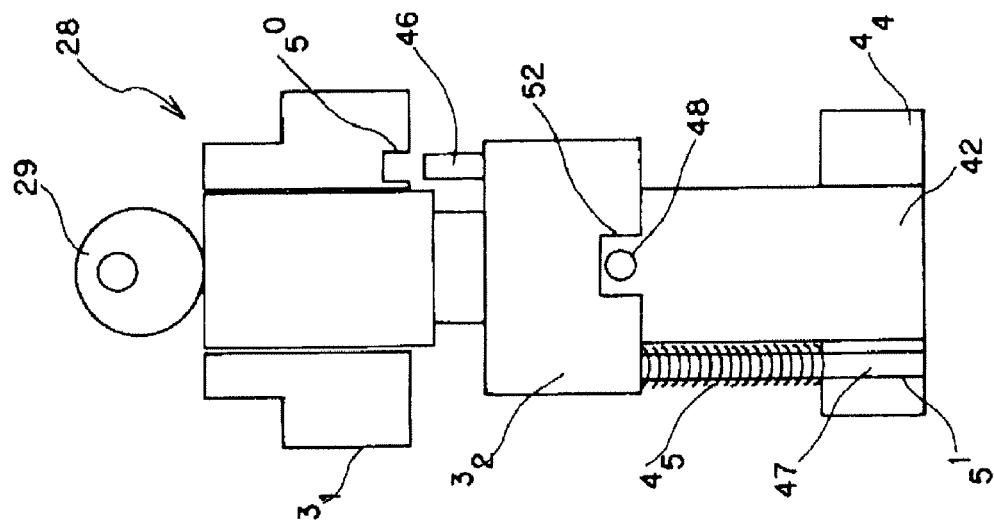

FIGS. 8(a) & 8(b) each schematically show the operation of the switching mechanism of the centrifugal direction 28 of the microchip testing device. FIG. 8(a) shows the state of the centrifugation mode, in which the vertical shaft 32 is located down. FIG. 8(b) shows the state of the switching mode of the centrifugal direction in which the vertical shaft 32 is up.

FIGS. 9(a), (b1), to FIGS. 11(b4), (b5) each schematically show the operating relationship of the centrifugal rotor 23, the main shaft gear 44 and the planetary gear 34 of the microchip testing device relative to one another. FIG. 9(a) shows the state of the centrifugation mode. FIG. 9(b1) to FIG. 11(b5) each show the state of the switching mode of the centrifugal direction.

As shown in FIG. 8(a), the vertical shaft 32 is down. In the state of the centrifugation mode, the main shaft coupling pin 48 which projects from the main shaft 42 engages the rotary control groove 52 of the vertical shaft 32 so that the vertical shaft 32 is controlled by the main shaft 42 and turned integrally with the main shaft 42. Since the motion of the main shaft gear 44 is controlled by the lower engagement pin 47, it turns integrally with the main shaft 42. As is shown in FIG. 9(b), therefore, the main shaft gear 44 turns with the same rotary speed as the centrifugal rotor 23. In the planetary gear 34, which is attached in the centrifugal rotor 23, therefore, relative motion does not occur. Rotation around the main shaft 42 can be accomplished without autorotation of the planetary gear 34. This means that the microchip 2 turns around the main shaft 42, centrifugal force acting when the vertical shaft 32 is located down; this leads to the centrifugation mode.

If proceeding from the state shown in FIG. 8(a), the direction reversing motor 30 is driven by the controller 40 and the cam 29 is turned by 180°, the vertical shaft 32 moves up due to the upwardly directed force by the spring 45. As is shown in FIG. 8(b), the vertical shaft 32 is attached and not turned by control of its motion by the slide bearing 31 mounted in the measurement chamber 19, when the vertical shaft 32 moves up, the rotary control groove 52 of the vertical shaft 32 is released from the main shaft coupling pin 48 and the upper engagement pin 46 is inserted into the groove 50 for the upper engagement pin of the slide bearing 31. The movement of the main shaft gear 44 is also controlled by the lower engagement pin 47 so that it is coupled to the measurement chamber 19, attached and not turned. In this connection, the main shaft gear 44 is coupled to the measurement chamber 19, attached and not turned. However, it goes without saying that the main shaft gear 44 can be attached and made not able to turn, besides by coupling to the measurement chamber 19, by coupling to a component which does not turn.

The movement of the microchip 2 is described below using FIG. 9(b1) to FIG. 11(b5), when the vertical shaft 32 is up for the switching mechanism of the centrifugal direction 28, as is shown in FIG. 8(b). FIG. 9(b1) shows the state in which the vertical shaft 32 is raised up. The main shaft gear 44 is attached and is not turning. However, since the planetary gear 34 is pivotally attached in the centrifugal rotor 23, it turns together with the centrifugal rotor 23. Since the planetary gear 34 engages the main shaft gear 44, the planetary gear 34 turns engaged to the main shaft gear 44 when the centrifugal rotor 23 is turning. This means that the planetary gear 34 executes planetary motion in which it autorotates around the planetary main shaft 42 and moreover turns around the main shaft 42.

FIG. 10(b2) shows the state in which the centrifugal rotor 23, proceeding from the state shown in FIG. 9(b1), has been turned by 90°. The planetary gear 34 is turned according to the rotation of the centrifugal rotor 23 around the main shaft 44 by 90°. Since the planetary gear 34 autorotates in engagement with the main shaft gear 44, the microchip 2 also turns by $\alpha°$. FIG. 10(b3) shows the state in which the centrifugal rotor 23 has been rotated by 180° from the state shown in FIG. 9(b1). The planetary gear 34 is turned around the main shaft by 180° according to the rotation of the centrifugal rotor 23. Since the planetary gear 34 autorotates engaged with the main shaft gear 44, the microchip 2 is turned by $2\alpha°$.

FIG. 11(b4) shows the state in which the centrifugal rotor 23 has been rotated by 270° from the state shown in FIG. 9(b1). The planetary gear 34 is turned around the main shaft 42 by 270° according to the rotation of the centrifugal rotor 23. Since the planetary gear 34 autorotates engaged with the main shaft gear 44, the microchip 2 also turns by 3α°. FIG. 11(b5) shows the state in which the centrifugal rotor 23 has been rotated by 360° from the state shown in FIG. 9(b1), that is, has executed a full revolution. The planetary gear 34 is turned by 360° according to the rotation of the centrifugal rotor 23. Since the planetary gear 34 autorotates engaged with the main shaft gear 44, the microchip 2 also turns by 4α°.

As was described above, the microchip 2 can execute planetary motion in which it autorotates around the planetary main gear 43 and is also turned when the vertical shaft 32 is at the top; this leads to the switching mode of the centrifugal direction.

Proceeding from the state shown in FIG. 8(b), if the direction reversing motor 30 is again driven by the controller 40 and the cam 29 is turned by 180°, the vertical shaft 32 is pressed and moved down by the cam 29; this leads to the centrifugation mode shown in FIG. 8(a). In the state shown in FIG. 11(b5), there is switching to the centrifugation mode, the microchip 2 turns in the state turned by 4α° around the main shaft 42, by which the centrifugal force can act in the direction turned by 4α°. In this way, centrifugal force with different directions can act on the microchip 2 by controlling the main shaft gear 44 by means of the switching mechanism of the centrifugal direction 28 and by the switching operation of the centrifugal mode and of the switching mode of the centrifugal direction to one another.

One example is shown below in which the number of teeth of the planetary gear 34 is four times the number of teeth of the main shaft gear 44. Proceeding from the centrifugation mode shown in FIG. 8(a), the direction reversing motor 30 is driven by the controller 40, the vertical shaft 32 is moved up and switching operation to the switching mode of the centrifugal direction which is shown in FIG. 8(b) is carried out. In the switching mode of the centrifugal direction, the planetary gear 34 executes planetary motion in which it autorotates around the planetary main shaft 43 and also is turned around the main shaft 42.

As is shown in FIG. 10(b2), the planetary gear 34 is turned in a 90° rotation of the centrifugal rotor 23 proceeding from the state after the switching operation as shown in FIG. 9(b1) according to the rotation of the centrifugal rotor 23 around the main shaft 42 by 90° and executes autorotation by 22.5°. As is shown in FIG. 10(b3), the planetary gear 34 is turned in a 180° rotation of the centrifugal rotor 23 proceeding from the state after the switching operation as shown in FIG. 9(b1) according to the rotation of the centrifugal rotor 23 around the main shaft 42 by 180° and executes autorotation by 45°. As is shown in FIG. 11(b4), the planetary gear 34 is turned in a 270° rotation of the centrifugal rotor 23 proceeding from the state, after the switching operation as shown in FIG. 9(b1), according to the rotation of the centrifugal rotor 23 around the main shaft 42 by 270° and executes autorotation by 67.5°.

As is shown in FIG. 11(b5), the planetary gear 34 is turned in a 360° rotation, i.e., one full revolution, of the centrifugal rotor 23 proceeding from the state after the switching operation as shown in FIG. 9(b1) according to the rotation of the centrifugal rotor 23 around the main shaft 42 by 360° and executes autorotation by 90°. In the state shown in FIG. 11(b5), after one complete revolution of the centrifugal rotor 23, the direction reversing motor 30 is driven by the controller 40, the vertical shaft 32 is lowered, the rotary control groove 52 is caused to engage the main shaft coupling pin 48, and thus, switching operation to the centrifugation mode is performed. In FIG. 11(b5), the microchip 2 is in the state rotated by 90° proceeding from the state as shown in FIG. 9(b1). In the state shown in FIG. 11(b5), if there is switching to the centrifugation mode, the microchip 2 in the state turned 90° rotates around the main shaft 42 so that the centrifugal force is also acting in the direction turned by 90°.

A case is shown below in which the rotary control groove 52 and the main shaft coupling pin 48 are located diagonally to the radial directions of the vertical shaft 32 and the main shaft 42, i.e., a case is shown in which the rotary control groove 52 and the main shaft coupling pin 48 are each located on an arc of the vertical shaft 32 and the main shaft 42 every 180°. The diagonal arrangement of the rotary control groove 52 and the main shaft coupling pin 48 relative to the radial directions of the vertical shaft 32 and the main shaft 42 in the state as shown in FIG. 10(b3) makes it possible to switch from the switching mode of the centrifugal direction to the centrifugation mode. In FIG. 10(b3), the microchip 2 is in the state turned by 45° from the state shown in FIG. 9(b1). In the state shown in FIG. 10(b3), if there is switching to the centrifugation model, the microchip 2 in the state turned by 45° rotates around the main shaft 42 so that the centrifugal force also acts in the direction turned by 90°.

In this way, the centrifugal force can act in states of the microchip 2 turned at different angles depending on the ratio of the number of teeth of the planetary gear 34 to the number of teeth of the main shaft gear 44 and on the arrangement of the rotary control groove 52 and the main shaft coupling pin 48. Thus, centrifugal force with different directions can be applied differently to the microchip 2.

In this connection, for the switching mechanism of the centrifugal direction 28, an example is shown in which the vertical shaft is moved up by the cam 29, and in which the vertical shaft 32 and the main shaft gear 44 are attached by the upper engagement pin 45. The following and the like can be imagined:

attachment by fitting of the cross section of the vertical shaft 32 to the cross section of the main shaft gear 44;
attachment of the vertical shaft 32 and of the main shaft gear 44 by a magnet;
by a clutch means; and
driving of the main shaft 42 and the main shaft gear 44 independent of one another and control of the rotation ratio.

Furthermore, it is advantageous to attach the vertical shaft 32 and the measurement chamber 19 to one another via the slide bearing 31. The main shaft 42 thus has an arrangement in which the two ends are supported. This increases the stiffness so that vibration by rotation of the centrifugal rotor 23 can be reduced.

A state was described above in which a pair of microchips 2 is held in the centrifugal rotor 23. However, only one microchip 2 can also be tested, the other microchip being used simply as weight for counterbalancing it. Furthermore, the number of microchips 2 which can be held in the centrifugal rotor 23 can be further increased.

Figure 12:
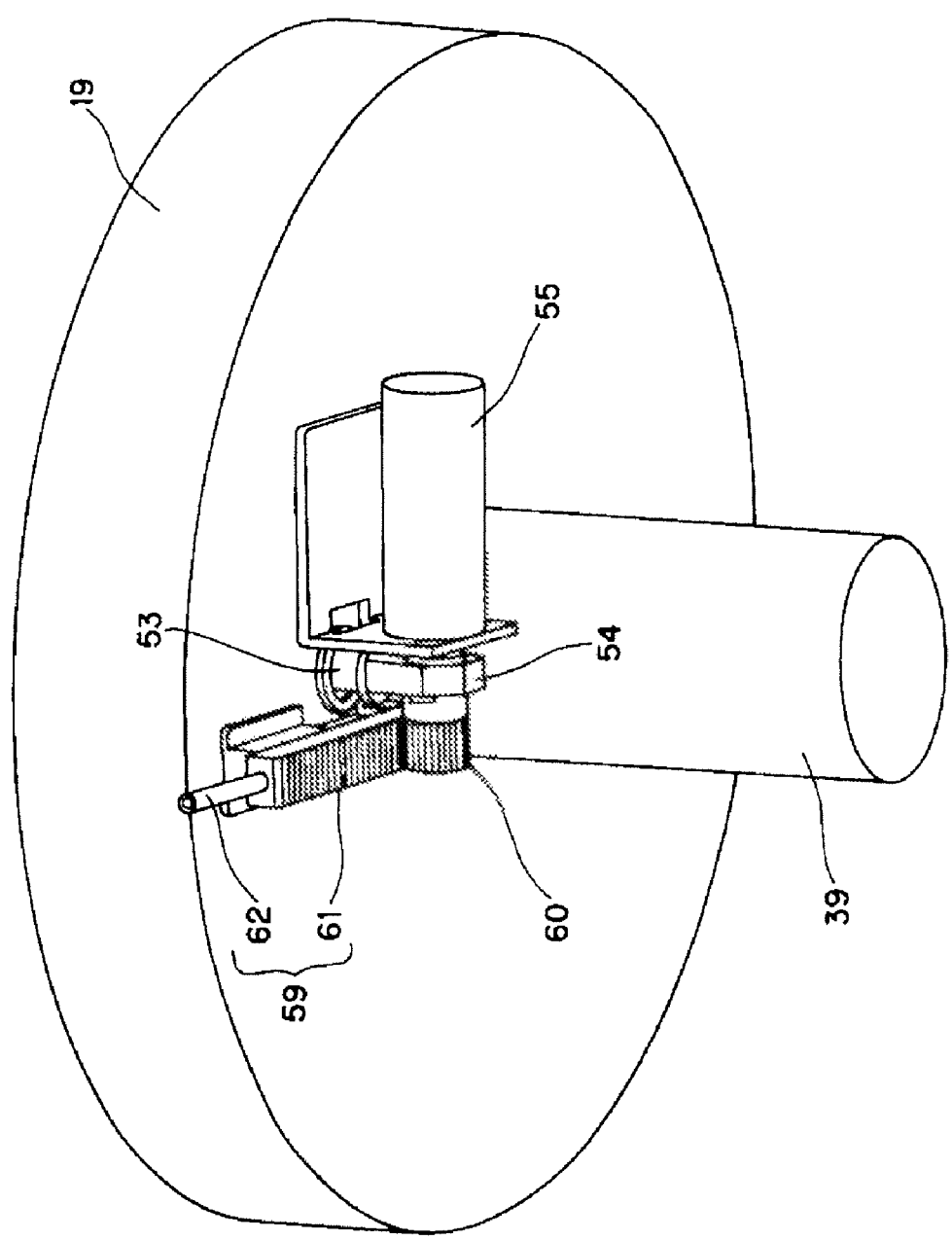
FIG. 12 is a schematic perspective view of the arrangement with a supporting part which supports the centrifugal rotor of the microchip testing device from underneath such that it can move up and down.
Figure 13:
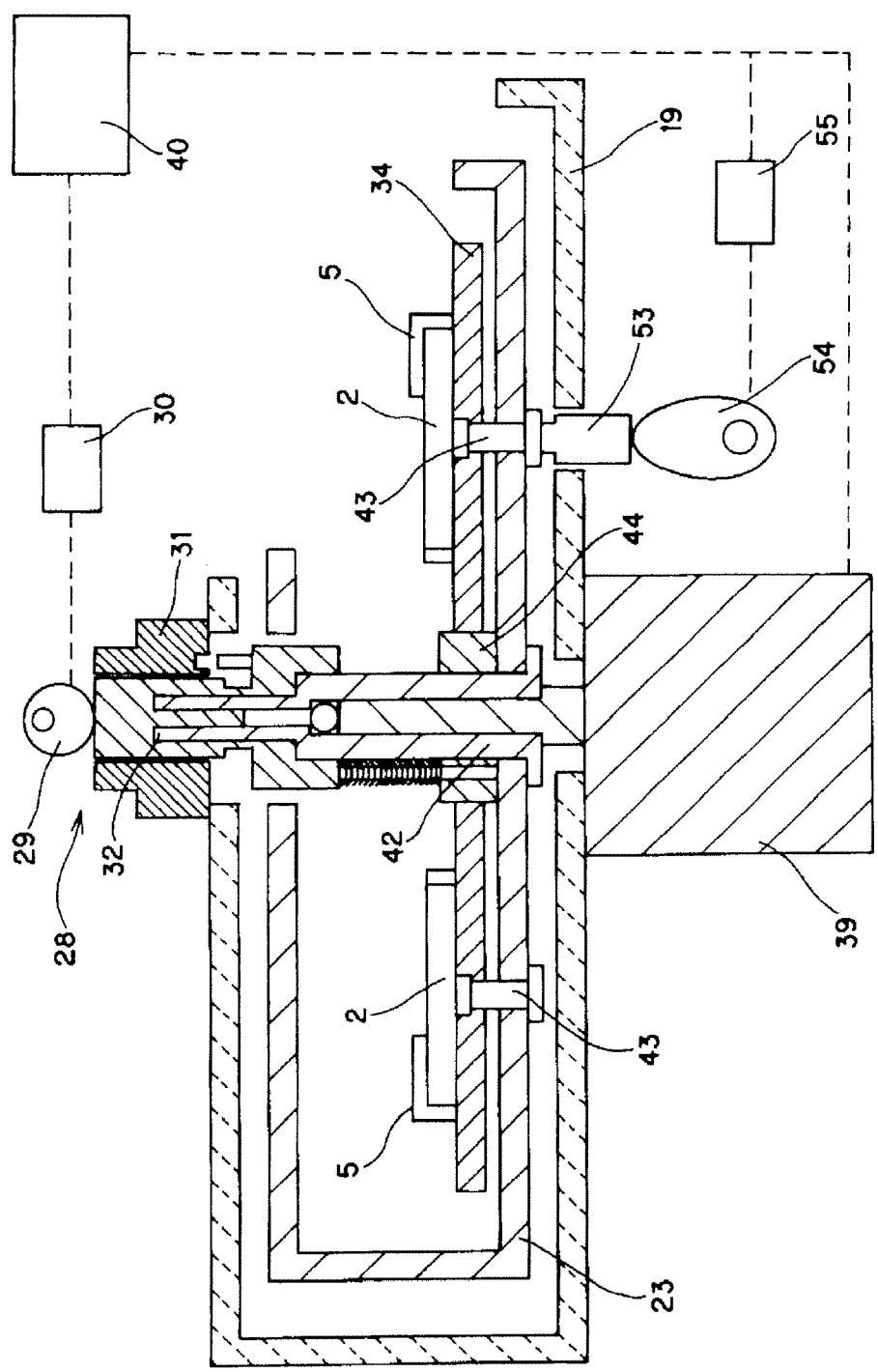
FIG. 13 is a schematic sectional view of the arrangement with a supporting part which supports the centrifugal rotor of the microchip testing device from underneath such that it can move up and down.

FIGS. 12 & 13 each show an arrangement with a supporting part 53 for supporting the centrifugal rotor 23 of the microchip testing device from underneath such that it can be moved up and down.

As described above, the microchip testing device positions the centrifugal rotor 23 by the rotary drive source 39 at a given location. The microchip 2 is removed from the microchip insertion part 4 or inserted into the microchip insertion part 4. In this insertion/removal of the microchip 2, when the cover 6 of the chip holder 5 is closed or in similar cases, force is applied down and is transmitted to the centrifugal rotor 23, it is possible for a load to be applied. If only a small load always arises at the same position in the same direction, there is the danger that the centrifugal rotor 23 will be deformed, that the bearing of the rotary drive source 39 will be damaged or that the axial equilibrium of the center axis of the centrifugal rotor 23 relative to the main shaft 42 will be lost. If the centrifugal rotor 23 deviates eccentrically, the light from the light source 35 will be obliquely incident in the microchip 2, by which the length of the optical path which is transmitted by the absorbance measuring part 10 is increased. Therefore, there is the possibility that incorrect test results will be output. That is, when the microchip 2 is inserted and removed an arrangement for supporting the chip holder 5 or the centrifugal rotor 23 is required to prevent a load from being applied to the centrifugal rotor 23.

As is shown in FIGS. 12 & 13, the supporting part motor 55 drives a supporting part drive part 54, and thus, moves the supporting part 53 up and down. The supporting part drive part 54 comprises a cam which moves the supporting part 53 into the blocking position by rotation and supports the centrifugal rotor 23 and preferably the center of gravity of the microchip 2, here, for the planetary main shaft 43, from underneath. When the microchip 2 is inserted and removed, the supporting part 53 is moved up to support the centrifugal rotor 23. By supporting the centrifugal rotor 23 in this way with the supporting part 53 from underneath, there is the action of suppressing the rotation of the centrifugal rotor 23 when the microchip 2 is inserted. The rotation of the centrifugal rotor 23 is released by the supporting part 53 being moved down. This means that the microchip 2 is moved to above the supporting part 53 by the controller 40 by driving of the supporting part motor 55, and afterwards, the chip is held in the chip holder 5. Then, the supporting part motor 55 is driven again and the supporting part 53 is moved down. Afterwards, the rotary drive source 39 is driven and rotation of the centrifugal rotor 23 is started. Then, after stopping the rotation of the centrifugal rotor 23 by the rotary drive source 39, the supporting part motor 55 is again driven, the supporting part 53 is moved up and afterwards the microchip 2 is removed from the chip holder 5.

Figure 14:
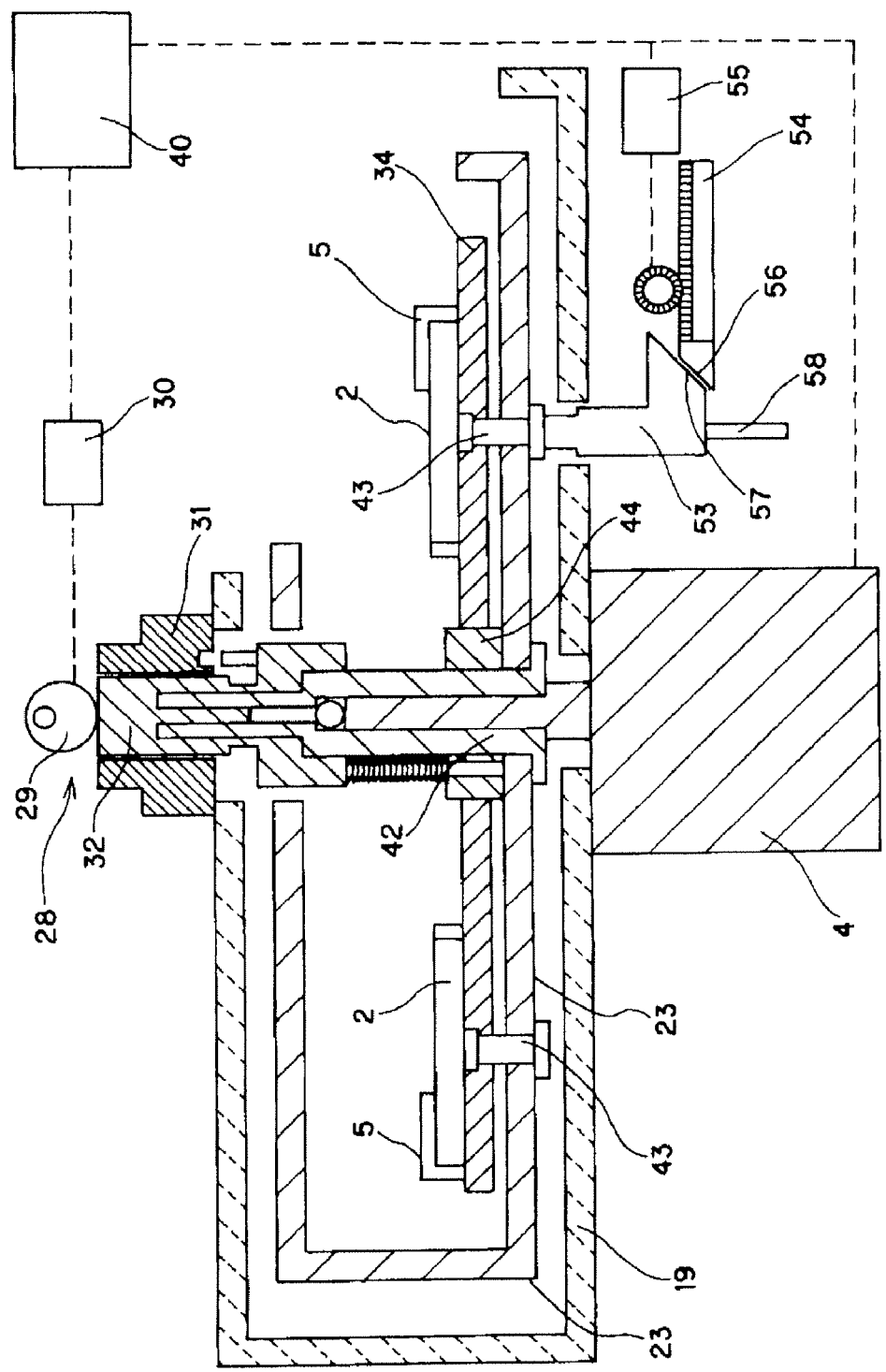
FIG. 14 shows a schematic of another arrangement with a supporting part which supports the centrifugal rotor of the microchip testing device from underneath such that it can move up and down.

FIG. 14 shows another arrangement with the supporting part 53 for supporting the centrifugal rotor 23 of the microchip testing device from underneath such that it can be moved up and down.

The arrangement of the supporting part 53 which can move up and down is not limited to the case in which the supporting part drive part 54 as shown in FIGS. 12 & 13 is used. That is, by converting the horizontal motion of the supporting part drive part 54 into vertical motion of the supporting part 53 by a slide surface 56 at the tip of the supporting part drive part 54 with a rack bordering the slide surface 57 underneath the supporting part 53, as is shown in FIG. 14, the supporting part 53 attached to the movable shaft 58 can be moved up and down. Furthermore, the supporting part 53, in the case in which the chip holder 5 is supported instead of the centrifugal rotor 23, also has the action that, when the microchip 2 is placed in the chip holder 5 and removed, no load is applied.

A lock part 59 for fastening the access cover 3 in the closed state in the process of testing by the microchip testing device is described below using FIG. 12. As is shown in FIG. 1, the body 1 is provided with an access cover 3 which is used for insertion/removal of the microchip 2. However, it is advantageous to fasten for safety that the access cover 3 does not open when the centrifugal rotor 23 turns. Therefore, the lock part 59 is put into place and is used to fasten such that the access cover 3 does not open. The lock part 59, for example, has a rack and is driven by the lock part driving part 60 which is continuously connected to the supporting part motor 55. The lock part 59 has a rack 61 which engages the lock part driving part 60, and a projection 62 in the form of an edge column or a cylindrical projection 62 which engages the side end of the body 1 of the rack 61.

When the supporting part motor 55 is being driven, the pinion gear of the lock part driving part 60 turns, by which the rack 61 moves in the direction away from the main shaft 42. The end of the projection 62 projects toward the side of the body 1. The closed state is fixed and maintained to prevent the cover 3 from being opened. Furthermore, if the lock part driving part 60 is turned such that the rack 61 moves in the direction to the main shaft 42, the end of the projection 62 enters the body 1. The access cover 3 can thus be returned to the state in which it can be opened/closed.

FIG. 15(a) is an outside view of the microchip 2 with an arrangement which differs from that of the microchip 2 as shown in FIG. 1. FIG. 15(b) is an enlargement of the cross section according to A-A' as shown in FIG. 15(a).

The microchip 2 shown in FIGS. 2(a) & 2(b) is a microchip for individual lot tests in which the part for measuring absorbance 10 is formed at only one location. FIG. 15(a) shows a microchip 2 for multi-lot tests in which several parts for measuring absorbance 10 are formed. The microchip 2 for multi-lot tests is, as shown in FIG. 15(b), produced by a transparent resin 8 being applied to the upper side and the lower side of a light-shielding resin 7. The part for measuring absorbance 10 of the microchip 2 vertically transmits light, by which analyses with the absorptiometry process are carried out.

Figure 15:
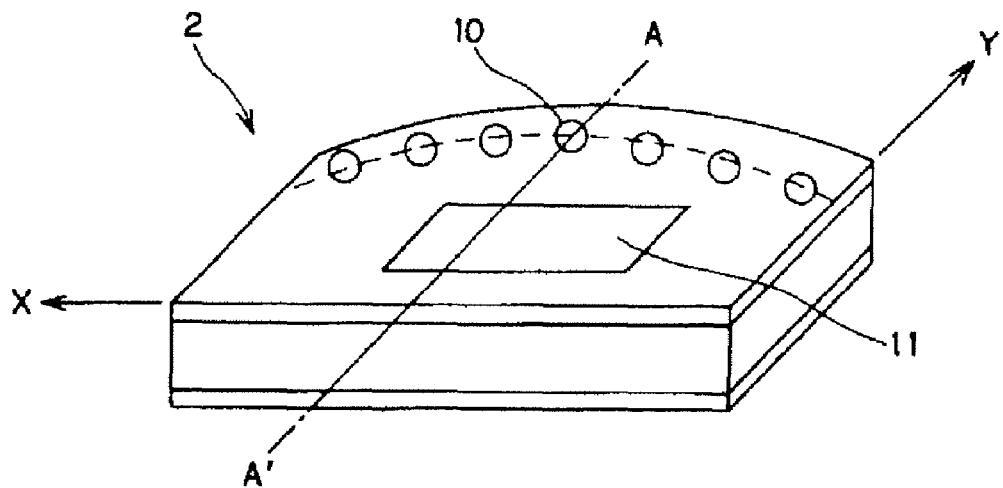
FIG. 15(a) is a perspective view of the microchip with a different arrangement than that of the microchip shown in FIG. 1.
FIG. 15(b) is an enlarged cross-sectional view of the microchip with a different arrangement than that of the microchip shown in FIG. 1.
Figure 15:
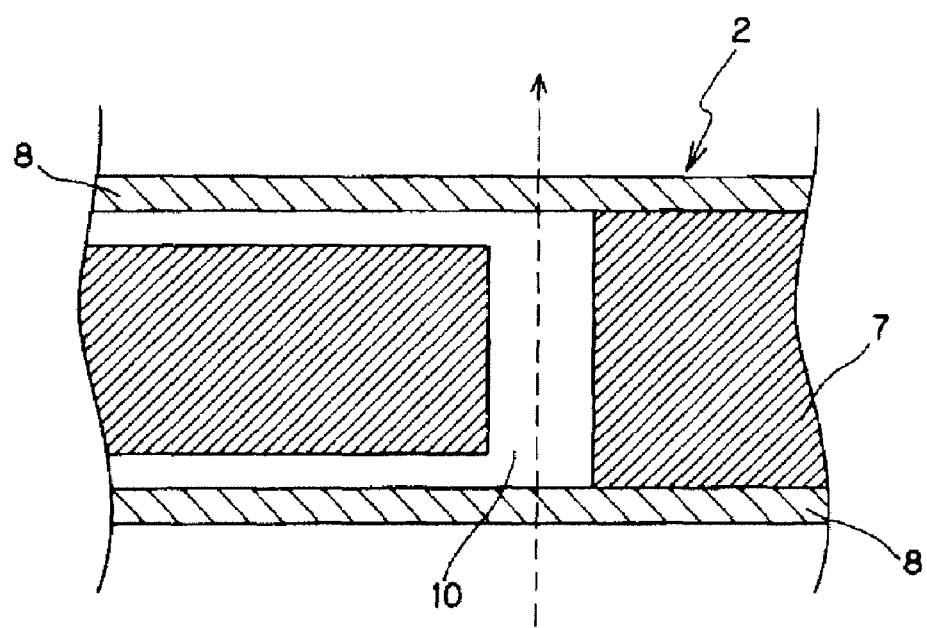
Figure 16:
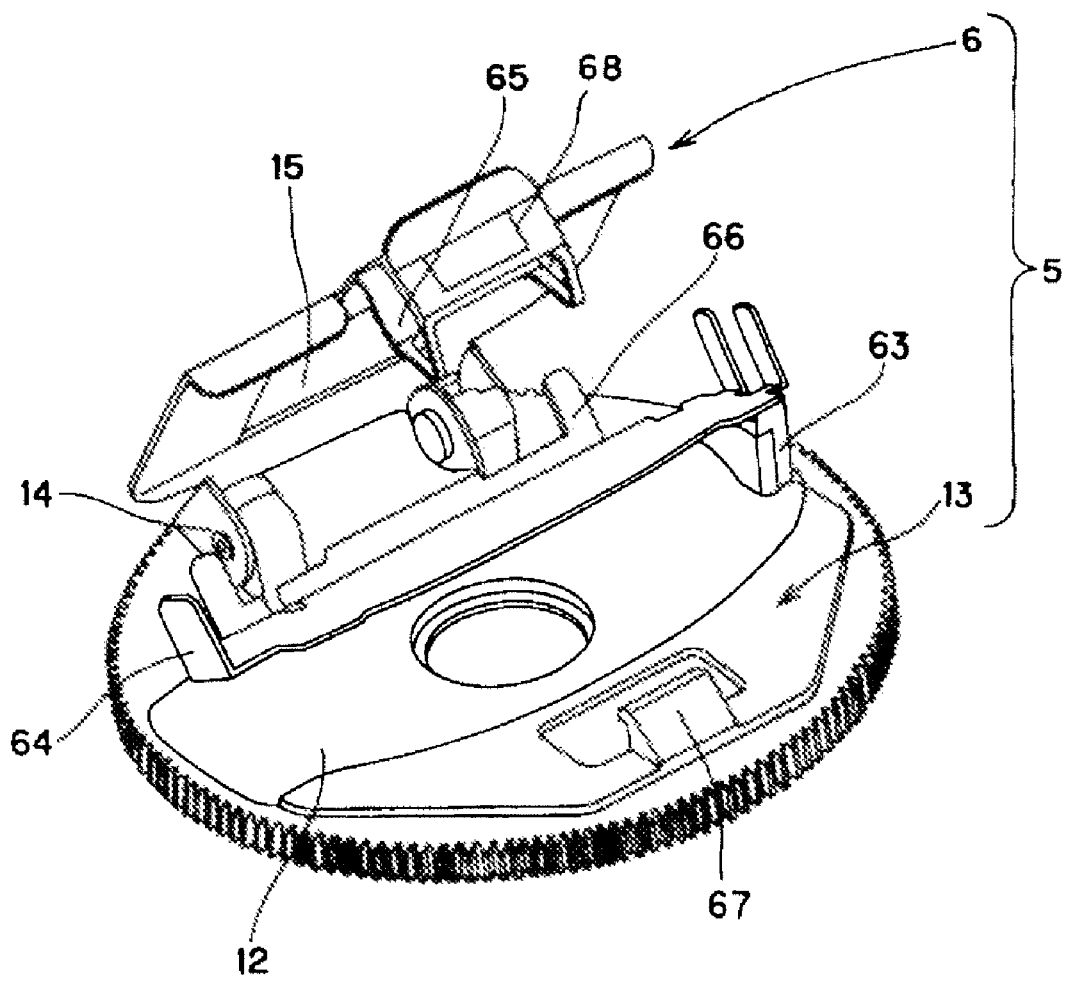
FIG. 16 is a perspective view of a chip holder which has an arrangement different than that of the chip holder shown in FIG. 3 and which is used as the microchip shown in FIG. 13(a)

FIG. 16 is an external view of the chip holder 5 which has an arrangement different than the chip holder 5 shown in FIG. 3 and which is used with the microchip 2 shown in FIG. 15(a). As is shown in FIG. 16, the chip holder 5 comprises a part 13 of resin which has a chip receiving space 12 in which the microchip 2 is held, and a metallic cover 6 which positions and attaches the microchip 2 at a given position. The cover 6 is attached at each articulation point 14 by means of a respective hinge. A code reader window 15 is provided in the cover 6 for reading the two-dimensional code 11 attached to the microchip 2 from the outside and a sample quantity sensor reading opening for checking whether the amount of sample added to the microchip 2 is sufficient or not are attached.

The chip holder 5 is fastened by a hook attachment opening 68 of the cover 6 being hooked to a hook 67 of the box 13 to prevent its opening when the chip holder 5 is exposed to a centrifugal force. The reason for this is that, when the chip holder 5 is turned with the microchip 2, it is exposed to a centrifugal force of over 400 G because, for example, one minute of rotation at 3000 rpm is needed to separate the blood sample added to the microchip 2 into plasma and blood cells.

Furthermore, the microchip 2 must be arranged stationary in the chip holding space 12 of the chip holder 5 with an accuracy tolerance within ±0.2 mm. The microchip 2 which is shown in FIG. 15 and which is held in the chip holder 5 is positioned and attached by a pin 63 of resin which located in the part 13, being pressed in the X direction against an X-reference surface 64 which is provided in the cover 6 and a compression spring 65 attached in the cover 6 being pressed against a Y reference surface 66 when the cover 6 is closed.

Figure 17:
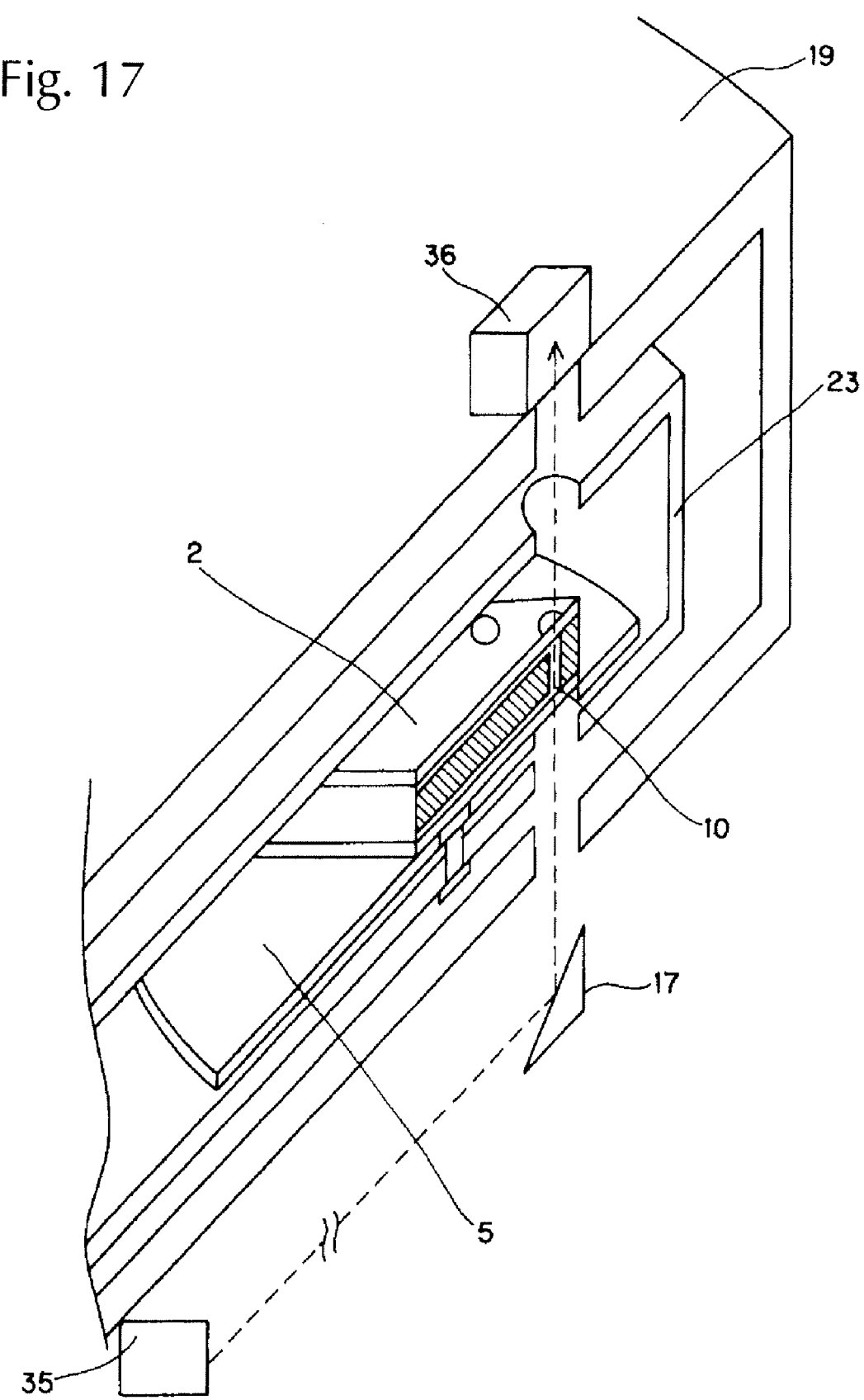
FIG. 17 is a perspective view, partially in cross section, of the arrangement of one example of the light source and a detector of a microchip testing device which is used with the microchip shown in FIG. 15(a)

FIG. 17 is a partial cross section of one example of the arrangement of the light source 64 and of the detector 65 of a microchip testing device which is used with the microchip 2 shown in FIG. 15(a). As is shown in FIG. 17, the light emerging from the light source 35 is converted, for example, by a lens or the like into parallel light. The parallel light is reflected by means of a mirror 17 and is transmitted vertically by the part for measuring absorbance 10 of the microchip 2. The transmitted light is received by the detector 36. By this arrangement of the light source 64 and of the detector 65, the chip holder 5 in which the microchip 2 for multi-lot testing is held can be mounted in the microchip testing device which is used for the microchip 2 for individual lot tests, and thus, analyses can be performed by means of the absorptiometry process.

Figure 18:
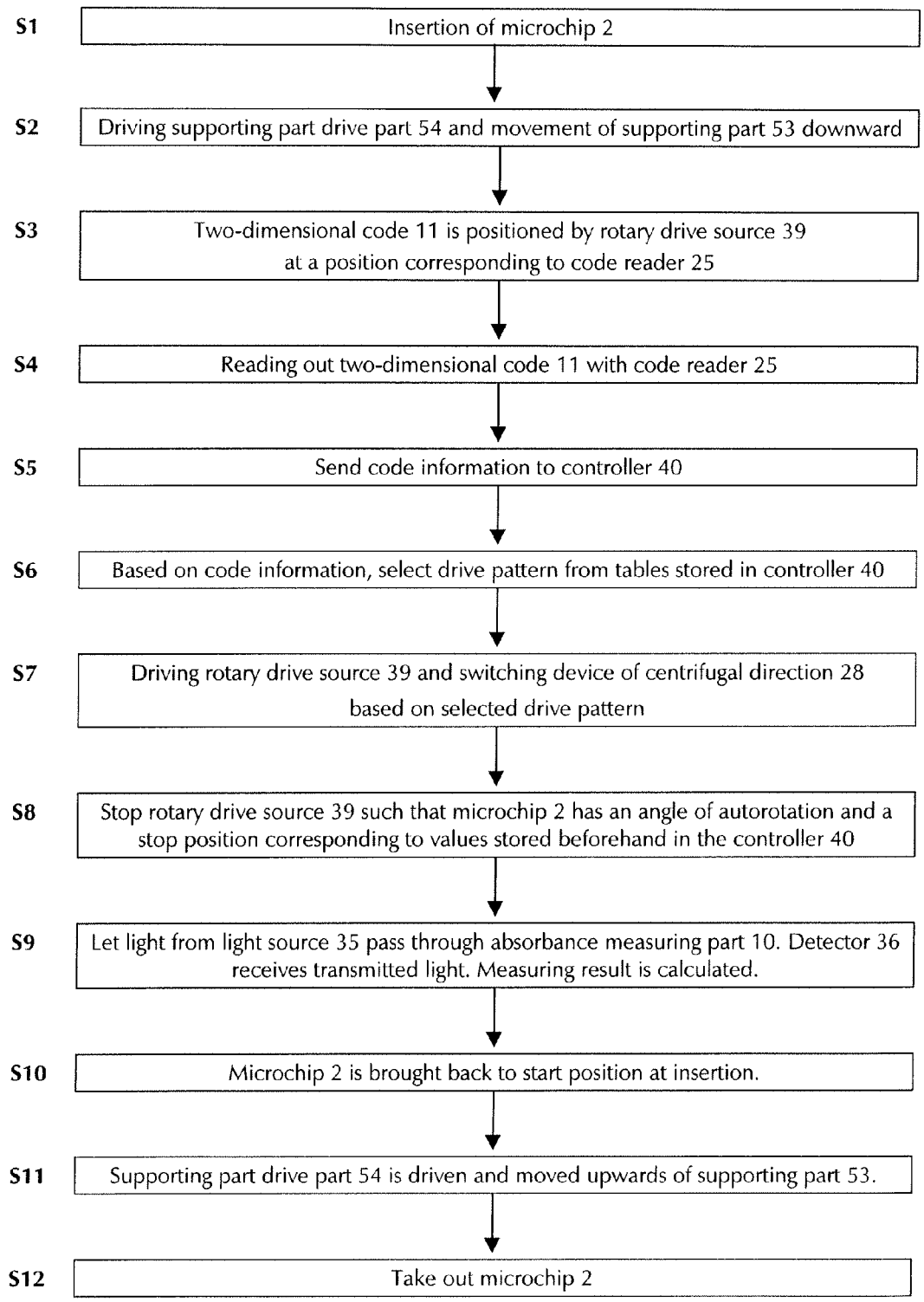
FIG. 18 is a flow chart of the sequence of actuation of the microchip testing device.

The actuation sequence of the microchip testing device is described below using the flow chart shown in FIG. 18. In FIG. 18 the procedure is as follows:

In step S1, the microchip 2 is received into the microchip testing device. Afterwards, in step S2, the supporting part drive part 54 is driven by the supporting part motor 55, by which the supporting part 53 is moved down. In step S3, the rotary drive source 39 turns the centrifugal rotor 23 by 130° and holds it. Thus, the two-dimensional code 11 is positioned at a location corresponding to the code reader 25 for reading. The code reader 25, in step S4, reads the two-dimensional code 11 attached to the microchip 2 through the code reader window 15. In step S5, the code information of the second two-dimensional code 11 which has been read in step S4 is sent to the controller 40. Based on the code information which has been sent to the controller 40 in step 5, in step S6, a drive pattern which is suited for the microchip 2 installed in the chip holder 5 is chosen from the tables stored in the controller 40.

The controller 40, in step S7, according to the drive pattern selected in step S6 drives the rotary drive source 39 and the switching mechanism of the centrifugal direction 28, determines the rotary velocity and the rotation time of the centrifugal rotor 23 in the centrifugation mode, and the direction of the centrifugal force which acts on the microchip 2, of the switching mechanism of the centrifugal direction 28, separates the blood into plasma and blood cells, mixes the plasma with the reagent, and thus, produces a sample liquid and feeds it to the part for measuring absorbance 10. Since the angle of autorotation of the chip holder 5 and the stop position of the centrifugal rotor 23 at which the part for measuring absorbance 10 of the microchip 2 is located is at a location corresponding to the light source 35 and the detector 36 stored beforehand, in step S8, in the controller 40, an indication to assume this position is delivered to the rotary drive source 39 and the switching mechanism of the centrifugal direction 28. Then the drive is stopped.

In step S9, the light from the light source 35 is transmitted by the part for measuring absorbance 10 of the microchip 2. The transmitted light is received by the detector 36. The concentration of the detection object component in the sample liquid of the part for measuring absorbance 10 is computed. In step 510, the microchip 2 is stopped by the rotary drive source 39 and the switching mechanism of the centrifugal direction 28 such that it assumes the same position as the initial position upon installation. In step S11, the supporting part drive part 54 is driven, by which the supporting part 53 is moved up. In step S12, the microchip 2 is removed form the chip holder 5.

Figure 19:
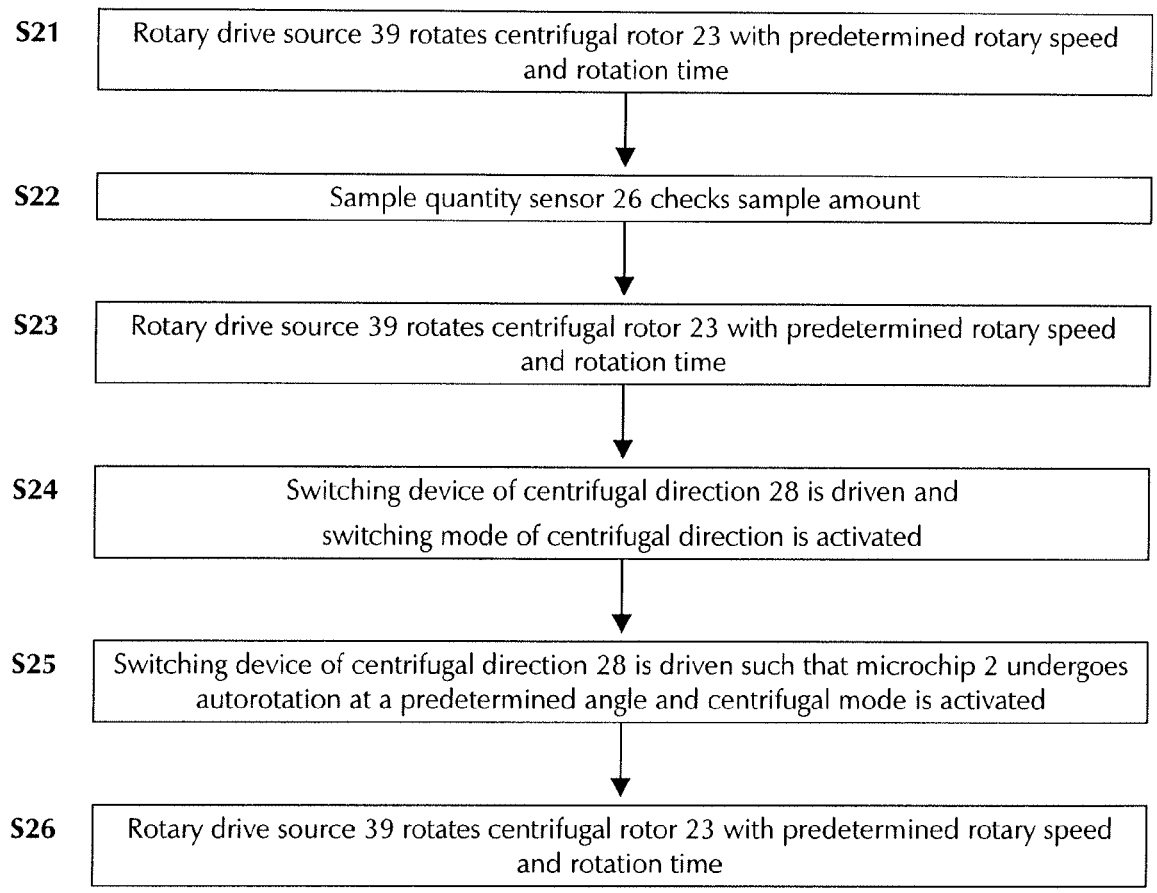
FIG. 19 is a flow chart of the sequence of actuation in the drive and switching step of the flow chart according to FIG. 18.

The flow chart in FIG. 19 shows the actuation sequence in the treatment of step S7 of the flow chart according to FIG. 18.

In FIG. 19, in step S21, the centrifugal rotor 23 is turned by the rotary drive source 39 with a given rotary velocity and rotation time, for example, at 2000 rpm for 15 seconds. The blood added to the microchip 2 is moved from the feed opening to the passage or the like. In step S22, the centrifugal rotor 23 is stopped by the rotary drive source 39 such that the sample quantity sensor reading opening 16 of the chip holder 5 is located at a position corresponding to the sample quantity sensor 26. The sample quantity sensor 26 assesses whether there is enough blood in the microchip 2 or not. In this connection, if the added blood is insufficient, the centrifugal rotor 23 is stopped and the measurement interrupted. When there is enough added blood, treatment according to step S23 is carried out.

In step S23, the centrifugal rotor 23 is turned by the rotary drive source 39 at a given rotational velocity and rotation time, for example, at 3000 rpm for 1 minute, and the blood is separated into plasma and blood cells. Depending on the shape of the passage and the type of reagent and the like, based on the code information, the direction and amount of centrifugal force which is to act on the microchip 2 are determined. If necessary, treatments according to steps S24 to S26 are carried out.

In step S24, the direction reversing motor 30 is driven and the cam 29 turned by 180°, by which the vertical shaft 32 is moved up, the main shaft coupling pin 48 is separated from the rotary control groove 52 of the vertical shaft 32, the upper engagement pin 46 is inserted into the groove 50 for the upper engagement pin of the slide bearing 31, and a switching operation from the centrifugation mode to the switching mode of the centrifugal direction is carried out. The main shaft gear 44 is fixed and does not turn. Since the centrifugal rotor 23 turns together with the rotary drive source 39, relative motion arises in the planetary gear 34. The planetary gear 34 executes a peripheral planetary motion around the main shaft 42 by its executing autorotation around the planetary main shaft 43. Thus, the microchip 2 turns around the planetary main shaft 43 by which it can automatically execute autorotation. In this autorotation of the microchip 2, the rotary drive source 39 turns, for example, with a low speed of at most 120 rpm, at which no centrifugal force is acting on the microchip 2.

In step S25, the vertical shaft 32 is pressed by the cam 29 and moved down when the direction reversing motor 30 is driven and the cam 29 is turned by 180° when a state is reached in which the microchip 2 executes autorotation at the angle indicated by the controller 40. Since the main shaft coupling pin 48 which projects from the main shaft 42 engages the rotary control groove 52 of the vertical shaft 32, the vertical shaft 32 is controlled by the main shaft 42, by which it starts to turn integrally with the main shaft 42. Thus, the switching mode of the centrifugal direction is changed to the centrifugation mode.

In step S26, the centrifugal rotor 23 is turned by the rotary drive source 39 at 2000 rpm and 15 seconds. The centrifugal force acts in the state in which the microchip 2 has been turned by a prescribed angle. As a result, a centrifugal force can act on the microchip 2 with different directions. In the state of the sample liquid after completion of step S26, if the absorbance can be measured, the treatment shown in FIG. 18 is carried out in step S8 of the flow chart. Depending on the shape of the passage, the type of reagent and the like, the direction of the centrifugal force applied to the microchip 2 is changed again based on the code information. If rotation of the centrifugal rotor 23 is necessary, there is a return to step S24 for treatment.

The actuation sequence of treatment in which the angle of autorotation of the chip holder 5 and the stop position of the centrifugal rotor 23 are corrected, in which the aperture part 18 of the chip holder 5 is located at a position corresponding to the detector 36, is described below using the flow chart shown in FIG. 20.

This correction treatment is carried out in step S1 of the flow chart according to FIG. 18 before the microchip 2 is received into the microchip testing device. First, in step S31 at the time at which the power source of the microchip testing device is turned on, i.e. in the heated-up state, the centrifugal rotor 23 is turned by the rotary drive source 39, furthermore the chip holder 5 undergoes autorotation and is stopped at a prescribed position which is stored in the controller 40 and to which the light source 35, the aperture part 18, a light passage opening which is not shown in the drawings, and the detector 36 correspond respectively.

In step S32, light emerges from the light source 35, the chip holder 5 being moved in the vicinity of the stop position. This light is received by the detector 36, and a light intensity signal is computed. In step S33, the stop position of the chip holder 5 at which the light intensity signal computed in step S32 constitutes the maximum value is stored in the controller 40. This is corrected as the angle of the autorotation stop position of the chip holder 5 used to measure the absorbance. By this correction of the stop position of the chip holder 5 measurements of the absorbance can be taken with measures against irregularities of the microchip testing device such as installation errors of the microchip 2, eccentricity and the like of the centrifugal rotor 23 and production faults of the chip holder 5 and the like.

With the microchip testing device in accordance with the invention, analyses by means of the absorptiometry process of the microchip can be carried out with a rotary drive source which can be stopped at a prescribed angle based on the indication of the controller, the light source from which the light is incident in the absorptiometry part of the microchip which is held in the chip holder, and the detector for receiving the light transmitted by the part for measuring absorbance and for computing the test result based on the amount of light received by it are located on the centrifugal rotor. Furthermore, test results are automatically obtained by operation of the microchip testing device because there is a controller for controlling the rotary drive source, the switching mechanism of the centrifugal direction and the part for measuring absorbance. Therefore, a special tester is not needed.

What is claimed is:

1. Microchip testing device, comprising:
   a rotary drive source which is stoppable at a prescribed angle;
   a centrifugal rotor which is connected to a main shaft which is turned by the rotary drive source;
   a centrifugal direction switching mechanism for controlling a concentric rotatable object which is freely fitted on the main shaft;
   a planetary revolution object which engages the concentric rotatable object which is located on the centrifugal rotor;
   a chip holder which is turnable together with the planetary revolution object;
   a microchip which is held in the chip holder and which has a part for measuring absorbance;
   a light source from which light is radiatable into the part for measuring absorbance of the microchip;
   a detector which receives light from the part for measuring absorbance; and
   a controller which controls movements of the rotary drive source and the centrifugal direction switching mechanism and stopping at a location at which absorbance measuring is performed corresponding to a location of the light source and detector;
   wherein the centrifugal direction switching mechanism has the following switching operation modes:
   a centrifugation mode in which the concentric rotatable object is connected to the rotary drive source and the planetary revolution object is turned without autorotation; and
   a switching mode in which the concentric rotatable object is connected to a measurement chamber and the planetary revolution object is subjected to planetary motion in which it is turned with simultaneous autorotation by the rotary drive source.

2. Microchip testing device in accordance with claim 1, wherein, underneath the centrifugal rotor, there is a supporting part which moves up and down, and a drive part for driving the supporting part, and wherein, when the supporting part moves up, the centrifugal rotor is supported by the supporting part.

3. Microchip testing device in accordance with claim 2, wherein the controller is adapted to first move the supporting part down, then start rotation of the centrifugal rotor, and after stopping the centrifugal rotor, to move the supporting part up.

4. Microchip testing device in accordance with claim 1, further comprising an access cover for enabling insertion and removal of a microchip in an open state and a lock part for engaging the access cover for placing the access cover in a locked closed state, and a lock part driving part for driving the lock part between a position placing the access cover in said open state and a position in which the access cover is maintained in said closed state by the locking part.

* * * * *